United States Patent [19]

Fried et al.

[11] 3,998,966
[45] Dec. 21, 1976

[54] ANTI-INFLAMMATORY, ANALGESIC, ANTI-PYRETIC AND ANTI-PRURITIC 6-SUBSTITUTED 2-NAPHTHYL ACETIC ACID DERIVATIVE-CONTAINING COMPOSITIONS AND METHODS OF USE THEREOF

[75] Inventors: John H. Fried; Ian T. Harrison, both of Palo Alto, Calif.

[73] Assignee: Syntex Corporation, Panama, Panama

[22] Filed: Mar. 17, 1975

[21] Appl. No.: 558,988

Related U.S. Application Data

[60] Division of Ser. No. 195,878, Nov. 4, 1971, Pat. No. 3,896,157, which is a division of Ser. No. 694,771, Dec. 7, 1967, abandoned, which is a continuation-in-part of Ser. No. 608,997, Jan. 13, 1967, abandoned.

[52] U.S. Cl. .............................. 424/308; 424/304; 424/317
[51] Int. Cl.$^2$ ................ A61K 31/235; A61K 31/19
[58] Field of Search ............ 424/317, 308; 260/469

[56] References Cited
UNITED STATES PATENTS

| | | | |
|---|---|---|---|
| 1,951,686 | 3/1934 | Wolfram | 260/108 |
| 3,663,584 | 5/1972 | Alvarez | 260/473 F |
| 3,681,432 | 8/1972 | Nelson | 260/473 F |

FOREIGN PATENTS OR APPLICATIONS
677,597  6/1968  South Africa

OTHER PUBLICATIONS
Elseivier's Encyclopedia of Org. Chem., Series III, vol. 12B, (1953), pp. 3276, 3310, 3311, 3325, 3326, 3338, 3412 & 3470.
Chemical Abstracts 62: 5238f (1965).
Chemical Abstracts 66: 114252le, (1967).

*Primary Examiner*—Leonard Schenkman
*Attorney, Agent, or Firm*—Joseph I. Hirsch; William B. Walker

[57] ABSTRACT

2-Naphthyl acetic acid derivatives and the corresponding amides, esters, hydroxamic acids and addition salts thereof, optionally substituted at the α-position on the acetic acid moiety and/or at position 6 and/or at positions 1, 4, 7 or 8 on the naphthyl ring and optionally saturated at positions 3 and 4, are anti-inflammatory, analgesic, anti-pyretic and anti-pruritic agents. A pharmaceutical method of effecting treatment of inflammation, pain, pyrexia and pruritus by the administration of naphthyl acetic acid derivatives. A pharmaceutical composition for use in the treatment of the above maladies comprising a naphthyl acetic acid derivative.

25 Claims, No Drawings

ANTI-INFLAMMATORY, ANALGESIC, ANTI-PYRETIC AND ANTI-PRURITIC 6-SUBSTITUTED 2-NAPHTHYL ACETIC ACID DERIVATIVE-CONTAINING COMPOSITIONS AND METHODS OF USE THEREOF

This is a division of application Ser. No. 195,878, filed Nov. 4, 1971 now U.S. Pat. No. 3,896,157, which, in turn, is a division of application Ser. No. 694,771, filed Dec. 7, 1967, now abandoned, which is a continuation-in-part of U.S. application Ser. No. 608,997 filed Jan. 13, 1967 now abandoned.

This invention relates to novel compositions useful as anti-inflammatory, analgesic, anti-pyretic and anti-pruritic agents. It also relates to novel methods for treating conditions marked by inflammation, pain, pyrexia, and pruritus. It further relates to novel compounds which are thus useful and to methods for their preparation, as well as to certain novel intermediates thereof.

The present compounds are derivatives of 2-naphthylacetic acid, a compound which can be represented by the formula:

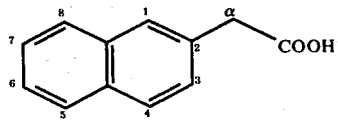

The arabic numerals and the alpha symbol indicate the positions used here in the nomenclature of 2-naphthylacetic acid derivatives.

The present invention more particularly pertains to a method of effecting treatment of inflammation, pain, pyrexia, and pruritus, as well as associative conditions thereof, by administering an effective quantity of a 2-naphthylacetic acid derivative as hereinafter defined or the corresponding amide, ester, hydroxamic acid or addition salt thereof, which salt is derived from a pharmaceutically acceptable non-toxic base.

These thus useful 2-naphthylacetic acid derivatives can be represented by the following formulas:

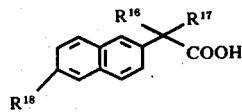

I

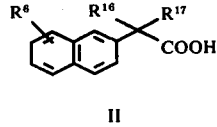

II

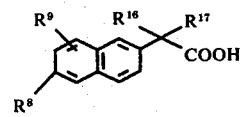

III

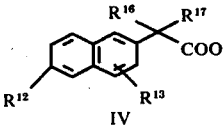

IV

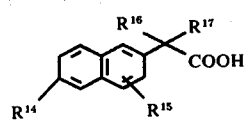

V

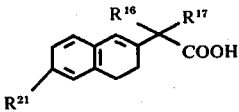

VI

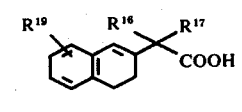

VII

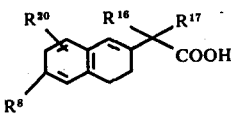

wherein each of $R^6$ (at position 1, 4, 7 or 8) and $R^{19}$ (at position 1, 7 or 8) is alkyl, trifluoromethyl, fluoro, chloro, hydroxy, conventional hydrolyzable ester, oxyether or thioether;

$R^8$ is alkyl, fluoro, chloro, hydroxy, conventional hydrolyzable ester, oxyether or thioether;

each of $R^9$ (at position 1, 4, 7 or 8) and $R^{20}$ (at position 1, 7 or 8) is alkyl, fluoro, chloro, hydroxy, conventional hydrolyzable ester, oxyether or thioether, provided that when $R^8$ is hydroxy, oxyether or thioether, $R^9$ or $R^{20}$ is the identical group or alkyl, fluoro, chloro or conventional hydrolyzable ester; provided that when one of $R^9$ or $R^{20}$ is hydroxy, oxyether or thioether, $R^8$ is the identical group or alkyl, fluoro, chloro, or conventional hydrolyzable ester;

each of $R^{12}$ and $R^{15}$ (at position 1 or 4) is hydroxy, oxyether or thioether;

each of $R^{13}$ (at position 1 or 4) and $R^{14}$ is alkoxy or alkylthio, provided when $R^{12}$ or $R^{15}$ is alkoxy or alkylthio, $R^{13}$ or $R^{14}$ respectively is a different alkoxy or alkylthio group;

one of $R^{16}$ and $R^{17}$ is hydrogen, the other being hydrogen, methyl, ethyl, difluoromethyl, fluoro or chloro; or $R^{16}$ and $R^{17}$ taken together are alkylidene, halomethylene or ethylene;

$R^{18}$ is hydrogen, alkyl, cycloalkyl, trifluoromethyl, hydroxymethyl, alkoxymethyl, vinyl, ethynyl, fluoro, chloro, hydroxy, conventional hydrolyzable ester, oxyether, thioether, formyl, carboxy, alkoxycarbonyl, acetyl, cyano or aryl;

$R^{21}$ is hydrogen, alkyl, cycloalkyl, trifluoromethyl, fluoro, chloro, hydroxy, conventional hydrolyzable ester, oxyether, thioether or aryl; and the corresponding amides, esters, hydroxamic acids and pharmaceutically acceptable addition salts thereof.

Several classes of novel naphthylacetic acid derivatives of formulas I—VIII include those of the following formulas:

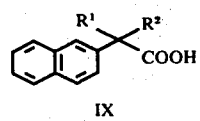

IX

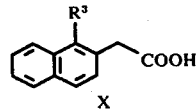

X

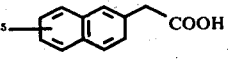

XII

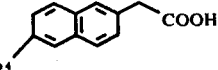

XI

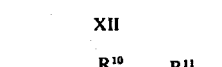

XIII

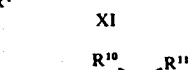

XIV

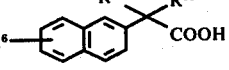

XVI

XV wherein one of $R^1$ and $R^2$ is hydrogen and the other is difluoromethyl, fluoro or chloro; or $R^1$ and $R^2$ taken together are alkylidene, halomethylene, or ethylene;

$R^3$ is trifluoromethyl, conventional hydrolyzable ester, difluoromethoxy, alkoxymethyloxy, 4'-alkoxytetrahydropyran-4'-yloxy, tetrahydrofuran-2'-yloxy, tetrahydropyran-2'-yloxy, or thioether;

$R^4$ is cycloalkyl, hydroxymethyl, alkoxymethyl, trifluoromethyl, vinyl, ethynyl, a conventional hydrolyzable ester, alkoxymethyloxy, alkylthiomethylthio, difluoromethoxy, alkoxymethylthio, alkylthiomethyloxy, difluoromethylthio, formyl, carboxy, alkoxycarbonyl, acetyl, cyano, or aryl;

each of $R^5$ (at position 4, 7 or 8) and $R^6$ (at position 1, 4, 7 or 8) is alkyl, trifluoromethyl, fluoro, chloro, hydroxy, conventional hydrolyzable ester, oxyether or thioether; provided that $R^5$ (when at position 7) is other than alkyl;

$R^7$ is alkyl, cycloalkyl, hydroxymethyl, alkoxymethyl, trifluoromethyl, vinyl, ethynyl, fluoro, chloro, hydroxy, conventional hydrolyzable ester, oxyether, thioether, formyl, carboxy, alkoxycarbonyl, acetyl, cyano or aryl;

each of $R^8$ and $R^9$ (at positions 1, 4, 7 or 8) is alkyl, fluoro, chloro, hydroxy, conventional hydrolyzable ester, oxyether or thioether; provided that when one of $R^8$ or $R^9$ is hydroxy, oxyether or thioether, the other is the identical group or alkyl, fluoro, chloro or conventional hydrolyzable ester;

one of $R^{10}$ and $R^{11}$ is hydrogen, the other being methyl, ethyl, difluoromethyl, fluoro or chloro; or $R^{10}$ and $R^{11}$ taken together are alkylidene, halomethylene, or ethylene; provided that when one of $R^{10}$ or $R^{11}$ is methyl or ethyl, $R^6$ (when at position 1 or 7) is other than alkyl; and the corresponding amides, esters, hydroxamic acids and pharmaceutically acceptable addition salts thereof.

By the terms which define an "alkyl" grouping are meant lower molecular weight, branched, or straight chain hydrocarbon groups of six or less carbon atoms, such as methyl, ethyl, propyl, isopropyl, butyl, tertbutyl, pentyl, hexyl, and the like. By the term "cycloalkyl" is meant cyclic hydrocarbon groups of three to seven carbon atoms, such as cyclopropyl, cyclopentyl, cyclohexyl, and the like.

By the term "alkoxy" is intended a straight or branched chain hydrocarbon ether group of six or less carbon atoms, including methoxy, ethoxy, 2-propoxy, butoxy, 3-pentoxy, and the like.

By the terms which define an "alkoxymethyloxy" grouping are meant methylether groups substituted with one alkoxy group; typical alkoxymethyloxy groups include methoxymethyloxy, ethoxymethyloxy, isopropoxymethyloxy, and the like.

By the term "alkylthio" is intended straight or branched chain hydrocarbon thioether groups of six or less carbon atoms, including methylthio, ethylthio, propylthio, 2-propylthio, 2-butylthio, pentylthio, 3-hexylthio, and the like.

The term "alkylthiomethyloxy" as used herein denotes methylether groups substituted with an alkylthio group; typical alkylthiomethyloxy groups include methylthiomethyloxy, 2-propylthiomethyloxy, pentylthiomethyloxy, and the like.

The term "alkylthiomethylthio" as used herein denotes methylthio ether groups substituted with an alkylthio group, including methylthiomethylthio, ethylthiomethylthio, and the like.

By the terms which define an "alkoxymethylthio" grouping are meant methylthio ether groups substituted with one alkoxy group, such as methoxymethylthio, ethoxymethylthio, 2-propoxymethylthio, and the like.

By the term "aryl" is intended unsubstituted and p-mono substituted phenyl derivatives, such as phenyl, p-tolyl, p-fluorophenyl p-chlorophenyl, p-hydroxyphenyl, p-methoxyphenyl, p-ethylphenyl, and the like.

By the term "halomethylene" is meant mono- or dihalomethylene groups wherein halo is fluoro or chloro. The preferred halomethylenes include fluoromethylene, difluoromethylene, fluorochloromethylene, and chloromethylene.

The term "conventional hydrolyzable ester" as used herein denotes those hydrolyzable ester groups conventionally employed in the art, preferably those derived from hydrocarbon carboxylic acids or their salts. The term "hydrocarbon carboxylic acid" defines both substituted and unsubstituted hydrocarbon carboxylic acids. These acids can be completely saturated or possess varying degrees of unsaturation (including aromatic), can be of straight chain, branched chain, or cyclic structure and, preferably, contain from one to twelve carbon atoms. In addition, they can be substituted by functional groups, for example, hydroxy, alkoxy containing up to six carbon atoms, acyloxy containing up to twelve carbon atoms, nitro, amino, halogeno and the like, attached to the hydrocarbon backbone chain. Typical conventional hydrolyzable esters thus included within the scope of the term and the instant invention are acetate, propionate, butyrate, valerate, caproate, enanthate, caprylate, pelargonate, acrylate, undecenoate, phenoxyacetate, benzoate, phenylacetate, diphenylacetate, diethylacetate, trimethylacetate, t-butylacetate, trimethylhexanoate, methylneopentylacetate, cyclohexylacetate, cyclopentylpropionate, adamantoate, glycolate, methoxyacetate, hemisuccinate, hemiadipate, hemi-$\beta,\beta$-dimethylglutarate, acetoxyacetate, 2-chloro-4-nitrobenzoate, aminoacetate, diethylaminoacetate, piperidinoacetate, $\beta$-chloropropionate, trichloroacetate, $\beta$-chlorobutyrate, and the like.

The term "oxyether" as used herein denotes those ether groups conventionally employed in the art, preferably those derived from normal chain, branched chain, aromatic hydrocarbons and oxo heterocyclic hydrocarbons. The term "hydrocarbon" defines both saturated and unsaturated hydrocarbons. Those designated hydrocarbons are optionally substituted with groups such as hydroxy, alkoxy, halo, alkylthio, and the like. Preferably the hydrocarbons contain from one to twelve carbon atoms. Typical oxyethers thus include alkoxy, difluoromethoxy, alkoxymethyloxy, alkylthiomethyloxy, tetrahydrofuran-2'-yloxy, tetrahydropyran-2'-yloxy, and 4'-alkoxytetrahydropyran-4'-yloxy.

The term "thioether" as used herein denotes those ether groups conventionally employed in the art, preferably those derived from normal chain, branched chain, cyclic and aromatic hydrocarbons. The term "hydrocarbon" defines both substituted and unsubstituted hydrocarbons. These hydrocarbons are optionally substituted with groups such as hydroxy, alkoxy, alkylthio, halo and the like. Preferably the hydrocarbons contain from 1 to 12 carbon atoms. Typical thioethers thus include alkylthio, difluoromethylthio, alkoxymethylthio, alkylthiomethylthio, and the like.

Also included within the scope of the present invention are the corresponding amides, esters, hydroxamic acids, and addition salts of the present 2-naphthylacetic acids.

In the preferred embodiment of this invention, the amides, esters, hydroxamic acids, or addition salts of the present 2-naphthylacetic acid derivatives are the preferred derivatives when the 2-naphthylacetic acid derivatives are substituted with tetrahydrofuran-2'-yloxy, tetrahydropyran-2'-yloxy, 4'-alkoxytetrahydropyran-4'-yloxy, alkylmethylenedioxy, alkylthiomethyleneoxy, alkoxymethylthio, or alkylthiomethylthio.

The amides of the present novel compounds are derived from conventional bases, such as ammonia, methylamine, ethylamine, methylethylamine, dimethylamine, diethylamine, pyrrolidine, piperidine, piperazine, N-ethylpiperazine, morpholine, di(methoxymethylene)amine, isopropylamine, aniline, N-methyl-N-cyclopentylamine, and the like. The amides are prepared by conventional means known to the art, for example, by treating the naphthylacetic acid derivative with thionylchloride, phosphorus pentachloride, and the like, and then treating the resulting acid chloride of the naphthylacetic acid derivative with an excess of ammonia or an amine.

The esters are also prepared by conventional techniques, such as by preparing the acid chloride of the 2-naphthylacetic acid derivative and then allowing the acid chloride to react with an alkanol, such as methanol, ethanol, and the like; or by treating the 2-naphthylacetic acid derivative with a diazoalkane, for example, diazomethane, diazoethane, and the like; or with an alkanol of 1 to 12 carbon atoms, for example, methanol, ethanol, butanol, or 3-pentanol, in the presence of an acid catalyst such as borontrifluoride, p-toluenesulfonic acid, or the like.

The hydroxamic acid derivatives are prepared by treating the 2-naphthylacetic acid ester derivatives with hydroxylamine (usually as the hydrochloride salt) in the presence of base, such as sodium methoxide, in an alkanol solvent, such as methanol, ethanol, and the like.

The addition salts are prepared by conventional techniques from pharmaceutically acceptable non-toxic bases, including metal salts such as sodium, potassium, calcium, aluminum, and the like, as well as organic amine salts, such as triethylamine, 2-dimethylamino ethanol, 2-diethylamino ethanol, lysine, arginine, histidine, caffeine, procaine, N-ethylpiperidine, hydrabamine, and the like.

Of the compounds of formulas I–VIII of this invention (defined above), the preferred derivatives are those wherein each of $R^6$ (at position 1, 4, 7 or 8) and $R^{19}$ (at position 1, 7 or 8) is fluoro, chloro, methyl, ethyl, isopropyl, methoxy, methoxymethyloxy, difluoromethoxy, 4'-methoxytetrahydropyran-4'-yloxy, methylthio, difluoromethylthio, or methoxymethylthio;

each of $R^8$, $R^9$ (at position 1, 4, 7 or 8) and $R^{20}$ (at position 1, 7 or 8) is fluoro, chloro, methyl, ethyl, isopropyl, methoxy, methoxymethyloxy, difluoromethoxy, 4'-methoxytetrahydropyran-4'-yloxy, methylthio, difluoromethylthio, or methoxymethylthio; provided that when one of $R^8$ and $R^9$ or one of $R^8$ and $R^{20}$ is hydroxy, oxyether or thioether, the other is the identical group, or methyl, ethyl, isopropyl, fluoro or chloro;

each of $R^{12}$, $R^{13}$ (at position 1 or 4), $R^{14}$ and $R^{15}$ (at position 1 or 4) is methoxy, difluoromethoxy, methoxymethyloxy, 4'-methoxytetrahydropyran-4'-yloxy, methylthio, difluoromethylthio or methoxymethylthio; provided that $R^{13}$ or $R^{14}$ is a different substituent than $R^{12}$ or $R^{15}$ respectively;

one of $R^{16}$ and $R^{17}$ is hydrogen, the other being hydrogen, methyl or difluoromethyl; or $R^{16}$ and $R^{17}$ taken together are methylene or difluoromethylene;

$R^{18}$ is hydrogen, methyl, ethyl, isopropyl, cyclopropyl, trifluoromethyl, vinyl, ethynyl, fluoro, chloro, methoxy, methoxymethyloxy, difluoromethoxy, 4'-methoxytetrahydropyran-4'-yloxy, methylthio, methoxymethylthio, or difluoromethylthio;

$R^{21}$ is hydrogen, methyl, ethyl, isopropyl, cyclopropyl, trifluoromethyl, methoxy, methoxymethyloxy, difluoromethoxy, 4'-methoxytetrahydropyran-4'-yloxy, methylthio, methoxymethylthio, or difluoromethylthio; and the corresponding amides, esters, hydroxamic acids and addition salts thereof.

When one of $R^1$ and $R^2$ or $R^{10}$ and $R^{11}$ or $R^{16}$ and $R^{17}$ is methyl, ethyl, difluoromethyl, fluoro or chloro, the present 2-naphthylacetic acid derivatives have an asymmetric carbon atom, the α-carbon atom of the acetic acid moiety. Accordingly, these compounds can exist as enantiomorphs. Each of the optical isomers of the present 2-naphthylacetic acid derivatives is included within the present invention. In some instances, one enantiomorph exhibits greater anti-inflammatory, analgesic, antipyretic and anti-pruritic activity, than the other enantiomorph.

The present 2-naphthylacetic acid derivatives that exist as enantiomorphs can be administered as mixtures of enantiomorphs or as resolved enantiomorphs.

The optical isomers can be resolved by conventional means, such as selective biological degradation; or by the preparation of diastereo-isomer salts of the 2-naphthylacetic acid derivatives with an alkaloid, such as cinchonidine, and the separation of the diastereo-isomers by fractional crystallization. The separated diastereo-isomer salts are acid cleaved to yield the respective optical isomers of the 2-naphthylacetic acid derivatives.

The above compounds have high therapeutic value in the treatment of various inflammatory conditions, such as of the skin, eyes, respiratory tract, bones, and internal organs, contact dermatitis, allergic reactions, and rheumatoid arthritis. In those cases in which the above conditions include pain, pyrexia, and pruritus, coupled with the inflammation, the instant compounds are useful for relief of these associative conditions as well as the principal condition. The instant compounds are in addition, however, useful for treating pain, pyrexia, pruritus, and other syndromes thereof per se, such as those arising from bone fracture, toothache, bacterial and virus infection, contact with poisonous material, neuralgia, neuritis, lacerations, contusions, abrasions, and the like.

The preferred manner or oral administration provides the use of a convenient daily dosage regimen which can be adjusted according to the degree of affliction. Generally, a daily dose of from 0.1 mg. to 20 mg. of the active compound per kilogram of body weight is employed. Most conditions respond to treatment comprising a dosage level in the order of 1 mg. to 5 mg. per kilogram of body weight per day. For such oral administration, a pharmaceutically acceptable non-toxic composition is formed by the incorporation of any of the normally employed excipients. These compositions take the form of solutions, suspensions, tablets, pills, capsules, powders, sustained release formulations, and the like.

In addition, these compounds can be administered in conjunction with other medicinal agents depending upon the specific condition being treated.

Thus, for example, a measure of anti-inflammatory activity according to the carrageenin induced edema assay of Winter et al., Proceeding of the Society for Experimental Biology and Medicine III, 544 (1962) shows 6-ethyl-2-naphthylacetic acid and 6-methoxy-2-naphthyl-α-methylacetic acid to have three times and greater than six times the activity of phenylbutazone, respectively. Similar standard assays to measure analgesic and anti-pyretic activities show 6-methoxy-2-naphthyl-α-methylacetic acid to be three times and seven times the activity of aspirin in these two respective categories.

The above compounds of the present invention can be readily prepared from known starting compounds.

One such method by which they can be prepared involves the reaction of an unsubstituted or substituted naphthalene with acetyl chloride in nitrobenzene in the presence of about three molar equivalents of aluminum chloride to afford the corresponding 2-acetylnaphthalene derivative. The resulting derivative is heated with morpholine in the presence of sulfur at 150° C; the resulting product is refluxed with concentrated hydrochloric acid to furnish the corresponding 2-naphthylacetic acid derivative.

The naphthalenes that are used in the above process can be illustrated by the following formulas:

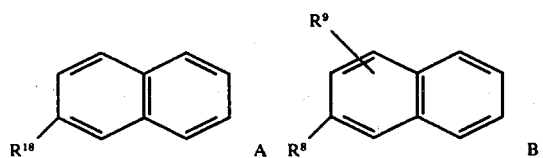

wherein $R^8$, $R^9$ and $R^{18}$ are as defined above.

The naphthalenes of formulas A and B are known to the art. Moreover, they can be prepared by conventional means. For example, 1,2-dimethoxybenzene is treated with succinic anhydride and aluminum chloride in a hydrocarbon solvent to afford 4-(3',4'-dimethoxyphenyl)-4-oxobutanoic acid. This is reduced by treatment with sodium borohydride, hydrogenolyzed by treating with palladium charcoal catalyst and hydrogen to furnish 4-(3',4'-dimethoxyphenyl) butanoic acid. The corresponding acid chloride is prepared such as by treatment with thionyl chloride, and the acid chloride is treated with aluminum chloride to afford 6,7-dimethoxy-1-tetralone. The tetralone is reduced and hydrogenolyzed by the means described above to furnish 6,7-dimethoxytetralin which is dehydrogenated by treating with palladium charcoal catalyst to afford 2,3-dimethoxy naphthalene. By utilizing 1-methyl-3-fluorobenzene in the above process, 6-methyl-8-fluoro-4-tetralone and 6-fluoro-8-methyl-4-tetralone (as intermediates) and 1-methyl-3-fluoro naphthalene and 1-fluoro-3-methyl naphthalene are prepared. The mixture of naphthalenes are separated by conventional means, such as vacuum distillation.

2-Alkyl, 2-cycloalkyl, or 2-aryl substituted naphthalenes, the naphthalenes of formula A wherein $R^{18}$ is alkyl or aryl, can be prepared from 2-tetralone by treating the latter with an equivalent of an alkyl, cycloalkyl or aryl magnesium bromide in an ether to obtain the corresponding 2-alkyl-, 2-cycloalkyl-, or 2-aryl-3,4-dihydronaphthalene which is dehydrogenated by heating with palladium charcoal catalyst to afford the corresponding 2-alkyl, 2-cycloalkyl, or 2-aryl naphthalene.

2-Vinyl naphthalenes are prepared by refluxing 2-ethyl naphthalenes with a molar equivalent of N-bromosuccinimide in a halohydrocarbon solvent, such as chloroform, methylene chloride, dichloroethane, carbontetrachloride, 1,4-dichlorobutane, chlorobenzene, chloroethane, chlorocyclohexane, dichlorobenzene, and the like, in light and in the presence of a trace amount of peroxide, such as benzoyl peroxide, t-butylperoxide, peroxyacetic acid, and the like, to afford the corresponding 2-(α-bromoethyl)-naphthalene. The latter is dehydrobrominated by treating with lithium carbonate in dimethylformamide to afford 2-vinylnaphthalene.

2-Ethynylnaphthalene is prepared from 2-vinylnaphthalene by brominating the latter in a halo hydrocarbon solvent and then debrominating the resulting 2-(α,β-dibromoethyl)naphthalene by conventional means, such as by treatment with sodium amide in liquid ammonia, to furnish the 2-ethynylnaphthalene.

2-Cyclopropylnaphthalene is prepared from 2-vinylnaphthalene by refluxing with diiodomethane in the presence of zinc: copper couple.

2-Cyclobutylnaphthalene is prepared from 2-naphthylmagnesium bromide by treating the latter with cyclobutanone to furnish 2-(1'-hydroxycyclobutyl)-naphthalene, which is hydrogenolyzed with hydrogen in the presence of Raney nickel to furnish 2-cyclobutylnaphthalene.

2-Cyclopentylnaphthalene can be prepared by heating naphthalene with cyclopentyl benzene sulfonate. 2-Cyclohexylnaphthalene an be similarly prepared by employing cyclohexyl benzene sulfonate.

2-Acetylnaphthalene is prepared by treating 2-(α-bromoethyl)-naphthalene, prepared as described above, with sodium acetate in acetic acid to afford 2-(α-ethanoyloxyethyl)-naphthalene which upon base hydrolysis furnishes the 2-(α-hydroxyethyl)-naphthalene. The latter is oxidized with an equivalent of chromium trioxide in glacial acetic acid or 8N sulfuric acid to furnish 2-acetylnaphthalene.

2-Carboxynaphthalene is prepared from 2-acetylnaphthalene by treating the latter with aqueous sodium hypochlorite. The 2-carboxy group is esterified by conventional means, described herein, to furnish 2-alkoxycarbonylnaphthalenes. By treating the latter with one equivalent of an alkali metal hydroxide, treating the resulting product with diborane in an ether, such as diglyme, (dimethoxydiethyleneglycol), 2-hydroxymethylnaphthalene is prepared.

The 2-hydroxymethyl group is esterified and etherified by conventional means employed to esterify and etherify primary hydroxy groups.

2-Formylnaphthalene is prepared from 2-hydroxymethylnaphthalene by treating the latter with manganese dioxide in a halo hydrocarbon solvent.

2-Cyanonaphthalenes are prepared by refluxing 2-formylnaphthalene with hydroxylamine hydrochloride and sodium acetate in ethanol to furnish the corresponding oxime which is refluxed with acetic anhydride in the presence of an acid catalyst to furnish 2-cyanonaphthalene.

Alternatively, the above substituents can be introduced on a naphthylacetic acid ester derivative by using an ethyl or vinyl substituted naphthylacetic acid ester derivative as a starting material.

In the preferred embodiment of the present invention, the starting materials are not substituted with trifluoromethyl, difluoromethoxy, difluoromethylthio, methylmethylenedioxy, alkoxymethylthio, alkylthiomethyloxy, alkylthiomethylthio, tetrahydropyran-2'-yloxy, tetrahydrofuran-2'-yloxy, or 4'-alkoxytetrahydropyran-4'-yloxy groups, but rather, such groups are introduced on the 2-naphthalene acetic acid derivative via one of the final steps.

Another method of preparing the present compounds employs unsubstituted and substituted 1-tetralones and can be illustrated by the following reaction sequence:

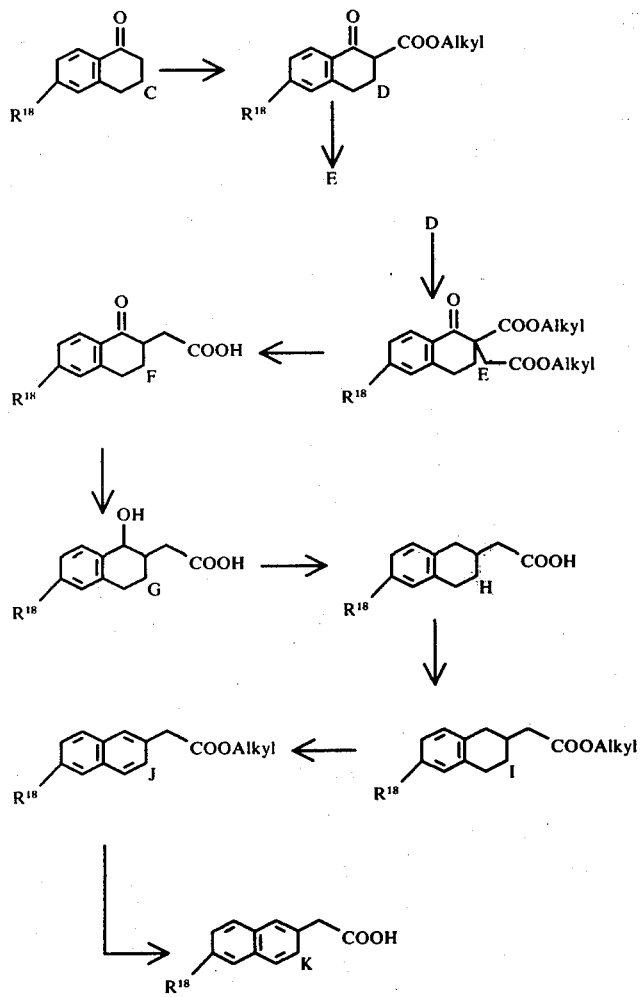

wherein alkyl and $R^{18}$ are defined as above.

The 1-tetralones, the compounds of formula C, are heated with two or more equivalents of a dialkyl carbonate, such as diethyl carbonate, in the presence of one or more equivalents of an alkali metal hydride, such as sodium hydride, potassium hydride, and the like, in a hydrocarbon solvent, such as hexane, cyclohexane, heptane, isooctane, benzene, toluene, xylene, and the like, to afford the corresponding alkoxy carbonyl compounds of formula D. The latter are treated with an alkali metal hydride in a hydrocarbon solvent; then the resulting products are treated with an α-haloacetic acid ester, such as ethyl α-bromoacetate, methyl α-iodoacetate, and the like, to furnish the corresponding 2-alkoxycarbonyl-2-(alkoxycarbonylmethyl)-1-tetralones, the compounds of formula E. The latter is hydrolyzed with an acid, such as hydrochloric acid, sulfuric acid, p-toluenesulfonic acid, and the like, to obtain the 2-(carboxymethyl) compounds of formula F. The latter is reduced with a reducing agent, such as sodium borohydride, lithium borohydride; or with one equivalent of hydrogen in the presence of Adam's catalyst, and the like, to afford the hydroxy compounds of formula G which are hydrogenolyzed by treatment with an equivalent amount of hydrogen in the presence of a hydrogenation catalyst, such as platinum, palladium, and the like, to furnish the corresponding 1,2,3,4-tetrahydro-2-naphthylacetic acid derivatives, the compounds of formula H. The compounds of formula H are esterified by conventional means, such as the means described above, to afford the compounds of formula I, which are dehydrogenated by heating with palladium charcoal catalyst at temperatures of 180° C and higher to furnish the corresponding 2-naphthylacetic acid ester derivatives, the compounds of formula J. The latter compounds are hydrolyzed to the corresponding 2-naphthylacetic acid derivatives, the compounds of formula K, by conventional hydrolysis, such as by treatment with an aqueous methanolic 5% sodium hydroxide solution.

Disubstituted tetralones of formula L are also employed in the above process to prepare the corresponding disubstituted 2-naphthylacetic acid derivatives of formula M:

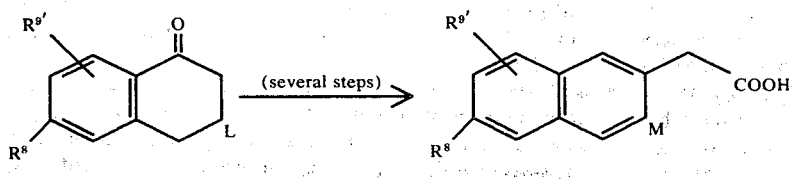

wherein R⁸ is as defined above and R⁹' respresents the same substituents as R⁹, but only at position 4, 7 or 8.

By treating the compounds of formula with an alkali metal hydride and then with an α-halocarboxylic acid ester, such as methyl α-bromopropionate and the like, the corresponding 2-alkoxycarbonyl-2-(α-alkoxycarbonylalkyl)-1-tetralones are obtained. These compounds can be hydrolyzed, reduced, hydrogenolyzed, esterified, dehydrogenated and hydrolyzed by the means used to similarly treat compounds of formula E, to obtain the corresponding 2-naphthyl-α-alkyl acetic acid derivatives.

The 1-tetralones of formulas C and L are prepared by conventional techniques, for example, such as the process used to make 6,7-dimethoxy-1-tetralone described above.

Alternatively, the 1-tetralones of formulas C and L can be prepared directly from naphthalenes by conventional means known to the art. For example, the substituted 1-tetralones can be prepared from substituted naphthalenes. The substituted naphthalenes are reduced with two molar equivalents of hydrogen in the presence of a platinum, palladium, nickel catalyst, or the like, to afford the corresponding substituted tetralin (hydrogenation of the unsubstituted ring is favored; when both rings are substituted, two products are obtained with different ring saturation). The substituted tetralin is then oxidized, such as with chromium trioxide in glacial acetic acid or 8N sulfuric acid, to obtain the substituted 1-tetralone.

The 1-tetralones substituted at positions 6 and 8 of formulas C and L can also be prepared from the corresponding 4-tetralones (which are intermediates in the above described preparation of naphthalenes substituted at positions 6 and 8) by reducing and hydrogenolyzing the latter with sodium borohydride and hydrogen in the presence of palladium respectively to afford the corresponding tetralins. The tetralins are then oxidized with chromium trioxide in acetic acid to afford the corresponding 1- and 4-tetralones substituted at positions 6 and 8. The tetralones are separated by conventional means, such as fractional crystallization or distillation.

1-Substituted and 1,6-disubstituted 2-naphthylacetic acid derivatives also can be prepared from 1-oxo-3,4-dihydro-2-[2H]naphthylacetic acid derivatives or 1-hydroxy-1,2,3,4-tetrahydro-2-naphthylacetic acid derivatives, the compounds of formula F or G respectively.

For example, the 1-chloro-2-naphthylacetic acid derivatives are prepared by first esterifying compounds of formula F by conventional means, such as described above, and then chlorinating the resulting 1-oxo esters by a conventional technique, such as by treatment with phosphorous pentachloride, to furnish the corresponding 1-chloro-3,4-dihydro compounds. The resulting 1-chloro products are then dehydregenated by conventional means, preferably by refluxing in a hydrocarbon solvent with 2,3-dichloro-5,6-dicyano-1,4-benzoquinone (DDQ) to furnish the corresponding 1-chloro-2-naphthylacetic acid derivatives.

The 1-fluoro-2-naphthylacetic acid ester derivatives are prepared by esterifying the carboxy group of the corresponding 1-hydroxy-1,2,3,4-tetrahydro-2-naphthylacetic acid derivatives, the compounds of formula G, and then treating the resulting ester with two or more equivalents of 1-diethylamino-1,2,2-trifluoro-2-chloroethane in a halogenated hydrocarbon solvent to afford the corresponding 1-fluoro derivative. The latter upon treatment with DDQ, as described above, affords the corresponding 1-fluoro-2-naphthylacetic acid ester derivative.

By treating the 1-oxo-3,4-dihydro-2-[2H]naphthylacetic acid ester derivatives with an alkyl magnesium bromide, such as methyl magnesium bromide, in a non-aqueous ether, such as diethylether, diisopropylether, dioxane, tetrahydrofuran, and the like, hydrolyzing the resulting products under acidic conditions, and then dehydrogenating the resulting 1-alkyl-1,2,3,4-tetrahydro-2-naphthylacetic acid ester derivatives by conventional techniques, such as the techniques described above, the corresponding 1-alkyl-2-naphthylacetic acid derivatives are obtained.

1-Alkoxy-2-naphthylacetic acid ester derivatives are prepared by treating 1-oxo-3,4-dihydro-2-[2H]naphthylacetic acid ester derivatives with an alkylorthoformate, such as methylorthoformate, in the presence of an acid catalyst, such as the ones described above, in a hydrocarbon solvent and then dehydrogenating the resulting 1-alkoxy-3,4-dihydro-2-naphthylacetic acid derivatives by conventional means, such as described above.

1-Alkylthio-2-naphthylacetic acid ester derivatives can be prepared by hydrolyzing a 1-alkoxy-2-naphthylacetic acid ester derivative to obtain the corresponding 1-hydroxy derivatives and then treating the latter with an alkylmercaptan, such as methylmercaptan, ethylmercaptan, and the like, in an acid environment at about 180° C under pressure greater than atmospheric pressure for 3 hours or more.

The 1-substituted-2-naphthylacetic acid ester derivatives are hydrolyzed by conventional methods, such as by the means described above, to the free acids.

Another method for the preparation of 4-substituted 2-naphthylacetic acid derivatives involves the treatment of benzene with an equivalent of a 3-halocarbonyl dialkyl glutarate, such as dimethyl 3-chlorocarbonyl glutarate and two or more equivalents of aluminum chloride in a hydrocarbon solvent to afford the corresponding dialkyl benzoyl glutarate, which is reduced and hydrogenolyzed as the oxo-containing compounds above to afford the corresponding dialkyl 3-benzyl glutarate. The latter is hydrolyzed by conventional means and the resulting 3-benzyl glutaric acid is treated with concentrated sulfuric acid to afford the corresponding 1,2-dihydro-4-oxo-2-[3H]naphthylacetic acid derivative. The latter is reduced, halogenated, alkylated, esterified and dehydrogenated by the processes used to reduce, halogenate, alkylate, esterify and dehydrogenate the 1-oxo-3,4-dihydro-2-[2H]naphthylacetic acid derivatives described above, to obtain 4-chloro-, 4-fluoro-, 4-hydroxy-, 4-alkyl-, 4-alkoxy-, and 4-alkylthio-2-naphthylacetic acid derivatives. The 4-substituted-6-substituted-2-naphthylacetic acid derivatives are obtained by employing a monosubstituted benzene, such as methoxybenzene, in the above process.

Another method of preparing the 8-substituted 2-naphthylacetic acid derivatives involves treating an ester of phenylacetic acid with two or more equivalents of succinic anhydride and aluminum chloride in a nitrobenzene or carbon disulfide to afford the corresponding alkyl p-(3-carboxy-1-oxopropyl)phenylacetate derivative, which is reduced and hydrogenolyzed by treatment with an alkali borohydride and palladium charcoal catalyst, respectively, to afford the ester of p-(3-carboxypropyl)phenylacetic acid. The corresponding acid halide is prepared by treating the latter with a conventional halogenating agent, such as phosphorus tri- or pentabromide or -chloride or thionyl chloride. The resulting ester of p-(3-halocarbonylpropyl)-phenylacetic acid is treated with three or more equivalents of aluminum chloride in a hydrocarbon solvent to furnish the ester of 8-oxo-5,6-dihydro-2-[7H] naphthylacetic acid. This compound can be reduced, halogenated, alkylated, esterified and dehydrogenated by the processes described above to obtain the 8-chloro-, 8-fluoro-, 8-hydroxy-, 8-alkyl-, 8-alkoxy- and 8-alkylthio-2-naphthylacetic acid derivatives.

Another method by which the present compounds can be prepared involves the reaction of 2-tetralones with one or more equivalents of a 1-alkoxycarbonylalkylidene triphenyl phosphorane, such as 1-methoxycarbonylethylidene triphenyl phosphorane, to furnish the corresponding 2,2-(1-alkoxycarbonylalkylidene)-tetralin. The latter upon heating with palladium charcoal catalyst affords the corresponding 2-naphthylacetic acid ester derivative.

For this purpose, the 1-alkoxycarbonylalkylidene triphenyl phosphorane reactant is conveniently provided upon reaction of triphenylphosphine with a 2-halocarboxylic acid ester in an organic reaction medium followed by reaction with a base.

Thus, for example, by reacting 6-methoxy-2-tetralone with the triphenylphosphorane derived from ethyl 2-halopropionate, 2,2-(1'-carbethoxyeth-1',1'-ylidene)-6-methoxytetralin is prepared. Dehydrogenation thereof provides ethyl 6-methoxynaphthyl-α-methylacetate which upon hydrolysis affords 6-methoxynaphthyl-α-methylacetic acid.

Unsubstituted and substituted 2-tetralones of the following formulas can be utilized in the above process:

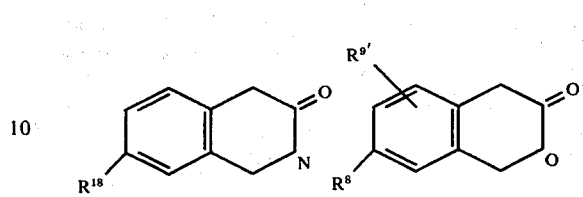

wherein $R^8$, $R^{9'}$ and $R^{18}$ are as defined above.

The substituted 2-tetralones of formulas N and O are prepared by treating the corresponding 1-tetralones with butylnitrite in ether and then esterifying the resulting 2-oximino-1-tetralones with an acid anhydride, such as acetic anhydride, in an organic acid, such as acetic acid, to obtain the substituted 2-acetylimino-2-tetralones. The acetylimino substituents are reduced to acetylamino substituents with hydrogen in the presence of palladium and the like. The keto groups are then reduced to hydroxy groups with sodium borohydride or the like. The substituted 2-acetylamino-1-hydroxytetralins are then treated with glacial acetic acid in the presence of concentrated acid to obtain the corresponding substituted 2-tetralones of formulas N and O.

The 3,4-dihydro-2-naphthylacetic acid derivatives of formulas VI, VII and VIII are prepared from the corresponding 2-naphthylacetic acid derivatives or the esters thereof by refluxing the latter in an alkanol with two or more equivalents of an alkali metal, such as lithium, potassium, sodium, and the like. Preferably the 2-naphthylacetic acid derivative starting material is not substituted with hydroxy or conventional hydrolyzable ester, but rather, these groups are introduced later by the means described herein.

The addition of an alkyl substituent at the α-position (with respect to the acetic acid chain) to obtain the 2-naphthyl-α-alkylacetic acid derivatives is optional, but when the addition is required, it is carried out following the preparation of the 2-naphthylacetic acid derivatives or the 3,4-dehydro derivatives thereof prepared as described above. The introduction of the α-alkyl substituents can be illustrated by the following reaction sequence:

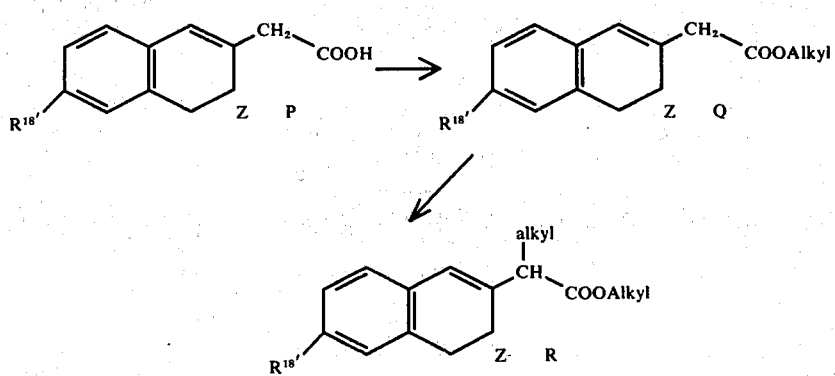

wherein $R^{18'}$ is alkyl, cycloalkyl, trifluoromethyl, vinyl, alkoxymethyl, fluoro, chloro, conventional hydrolyzable ester, oxyether, thioether, formyl, alkoxycarbonyl, acetyl, cyano or aryl;

Z is a carbon-carbon single bond or a carbon-carbon double bond; provided that when Z is a carbon-carbon double bond, $R^{18'}$ is alkyl, cycloalkyl, trifluoromethyl, fluoro, chloro, oxyether, thioether or aryl.

The 2-naphthylacetic acid derivatives, the compounds of formula P, are esterified by conventional means, such as being allowed to react with an alkanol in the presence of boron trifluoride, to afford the corresponding esters, the compounds of formula Q. The compounds of formula Q are treated with an alkali metal hydride such as sodium hydride, potassium hydride, and the like, in an ether solvent, such as monoglyme, and then with an alkyl halide, such as methyl iodide, to afford the corresponding 2-naphthyl-α-alkylacetic acid ester derivatives, the compounds of formula R. The latter are hydrolyzed by refluxing in a basic solution to obtain the corresponding 2-naphthyl-α-alkylacetic acid derivatives.

The ethynyl 2-naphthyl-α-alkylacetic acid derivatives are prepared from vinyl 2-naphthyl-α-alkylacetic acid derivatives by brominating and debrominating the latter's vinyl group by the means described above. Oxyether or alkoxymethyl 2-naphthyl-α-alkylacetic acid derivatives are hydrolyzed to obtain the hydroxy or hydroxymethyl derivatives respectively. Alkoxycarbonyl 2-naphthyl-α-alkylacetic acid derivatives are hydrolyzed to obtain the carboxy derivatives.

2-Naphthylacetic acid derivatives substituted at other positions are also employed in the above process.

The α-alkyl substituents are similarly introduced into other 2-naphthylacetic acid derivatives substituted at positions 1, 4, 7, 8 and/or 6. Prior to the above process, hydroxy groups are etherified and carboxy groups are esterified to protect them from attack by reagents used in subsequent elaborations. Such protected groups can be regenerated by hydrolysis after the process.

The introduction of other substituents on the α-carbon atom of the acetic acid moiety is also optional, but when carried out, is preferably done after the preparation of the 2-naphthylacetic acid derivatives and the esters thereof (including the 3,4-dihydro derivatives).

The α-difluoromethyl group can be introduced by treating the 2-naphthylacetic acid ester derivatives with an alkali metal or alkali metal hydride in a dialkyl carbonate, such as diethyl carbonate, to afford the corresponding α-alkoxycarbonyl derivatives. The latter is treated with chlorodifluoromethane and an alkali metal alkoxide, such as potassium t-butoxide, in an ether solvent, preferably 1,2-dimethoxyethane to afford the corresponding α-alkoxycarbonyl-α-difluoromethyl derivatives, which are hydrolyzed to furnish the corresponding 2-naphthyl-α-carboxy-α-difluoromethylacetic acid derivatives. The deesterified product is decarboxylated by heating to between 30° C and 150° C, until the evolution of carbon dioxide ceases to give the corresponding 2-naphthyl-α-difluoromethylacetic acid derivatives.

By treating the above 2-naphthyl-α-alkoxycarbonylacetic acid ester derivatives with an equivalent of an alkali metal hydride in a hydrocarbon solvent, then with an alkyl halide, the corresponding 2-naphthyl-α-alkoxycarbonyl-α-alkylacetic acid ester derivatives are obtained. The latter are hydrolyzed and decarboxylated to furnish the corresponding 2-naphthyl-α-alkylacetic acid derivatives. This is an alternative method of introducing the α-alkyl substituent.

The α-fluoro group is introduced by treating the 2-naphthylacetic acid ester derivatives with two or more equivalents of an alkyl formate, such as ethylformate, and three or more equivalents of an alkali metal or alkali metal hydride in a hydrocarbon solvent to afford the corresponding α-hydroxymethylene derivatives which are treated with an equivalent of an alkali metal hydride and one equivalent of perchloryl fluoride to afford the corresponding α-fluoro-α-formyl derivatives. The latter are oxidized by conventional means, such as with chromium trioxide in glacial acetic acid or 8N sulfuric acid, to furnish the corresponding α-fluoro-α-carboxy derivatives which are decarboxylated by heating to temperatures of 100° C or more to afford the corresponding 2-naphthyl-α-fluoroacetic acid ester derivatives. The corresponding α-chloro derivatives are prepared by utilizing chlorine in place of perchloryl fluoride in the above process.

The α,α-difluoromethylene group can be introduced by refluxing 2-naphthyl-α-chloroacetic acid ester derivatives with an alkali metal hydroxide in an alkanol to afford the corresponding 2-naphthyl-α-hydroxyacetic acid derivative. The carboxy groups of the latter are re-esterified by conventional methods and the resulting esters are then oxidized by conventional meas, such as described above, to obtain the corresponding α-oxo derivatives, which upon being refluxed with one equivalent of difluoromethylidene triphenylphosphorane in a hydrocarbon solvent, affords the corresponding 2-naphthyl-α,α-difluoromethyleneacetic acid ester derivatives. The corresponding α,α-fluorochloromethylene derivatives are prepared by using chlorofluoromethylidene triphenylphosphorane in place of difluoromethylidene triphenylphosphorane in the above process. The difluoromethylidene triphenylphosphorane is prepared by refluxing sodium chlorodifluoroacetate with triphenylphosphine in dimethylformamide. Similarly, triphenyl chlorofluoromethylidene phosphorane is prepared by employing sodium dichlorofluoroacetate.

The α,α-chloromethylene group can be introduced by treating 2-naphthyl-α,α-hydroxymethyleneacetic acid ester derivatives with phosphorus pentachloride in a hydrocarbon solvent.

The α,α-fluoromethylene group can be introduced by tosylating 2-naphthyl-α,α-hydroxymethyleneacetic acid ester derivatives with p-toluenesulfonyl chloride in a hydrocarbon solvent and then treating the resulting tosylate with an alkali metal fluoride, such as sodium fluoride. By utilizing an alkali metal chloride in the above process, the corresponding α,α-chloromethylene derivatives are furnished.

The α,α-methylene group is introduced by treating the 2-naphthyl acetic acid ester derivatives with formaldehyde or paraformaldehyde and an alkali metal alkoxide, such as sodium methoxide in dimethylsulfoxide.

The α,α-ethylene group is introduced by refluxing the 2-naphthyl-α,α-methyleneacetic acid ester derivatives with diiodomethane in the presence of zinc-copper couple in an ether solvent.

In the preferred embodiment of this invention the hydroxy, hydroxymethyl, conventional hydrolyzable ester, alkoxymethyloxy, alkylthiomethyloxy, tetrahydrofuran-2'-yloxy, tetrahydropyran2'-yloxy, 4'-alkoxytetrahydropyran-4'-yloxy, alkoxymethylthio and alkylthiomethylthio are introduced after the introduction of substituents at the α-position of the 2-naphthyl acetic acid derivatives.

Those compounds containing a trifluoromethyl group are preferably prepared from the corresponding methyl substituted 2-naphthylacetic acid ester derivatives by treating the latter with chlorine and phosphorus trichloride in the presence of light to afford the corresponding trichloromethyl derivatives, which, when refluxed with antimony trifluoride in a hydrocarbon solvent, furnish the corresponding trifluoromethyl substituted 2-naphthylacetic acid ester derivatives. In the preferred embodiment of the present invention the trifluoromethyl group is introduced on the 2-naphthylacetic acid derivatives starting material prior to the preparation of the corresponding 3,4-dihydro derivatives by the above described processes.

Those compounds containing difluoromethoxy groups are preferably prepared from the corresponding alkoxy substituted 2-naphthylacetic acid ester derivatives by refluxing the latter with 48% hydrobromic acid in acetic acid to furnish the free hydroxy derivatives which, upon treatment with chlorodifluoromethane and an alkali metal hydroxide in aqueous dioxane or tetrahydrofuran, affords the corresponding difluoromethoxy substituted 2-naphthylacetic acid ester derivatives.

By utilizing alkylthio 2-naphthylacetic acid ester derivatives in the above process, the corresponding difluoromethylthio derivatives are obtained.

The hydroxy groups are etherified by conventional methods, for example, by treatment with an alkali metal hydride and then with an alkylhalide, preferably an alkylbromide or iodide; or by treatment with a diazoalkane or an alkanol in the presence of borontrifluoride in an ether solvent, and the like.

The alkoxymethyloxy groups are introduced by treating the hydroxy substituted 2-naphthylacetic acid derivatives with an alkoxychloromethane in dimethylformamide to afford the corresponding alkoxymethyloxy substituted 2-naphthylacetic acid derivatives. The alkylthiomethyloxy substituted 2-naphthylacetic acid derivatives are prepared by utilizing an alkylthiochloromethane in the above process.

The alkoxymethylthio substituted 2-naphthylacetic acid derivatives are prepared by refluxing thio substituted 2-naphthylacetic acid derivatives with an alkoxychloromethane in dimethylformamide. The alkylthiomethylthio substituted derivatives are prepared by using an alkylthiochloromethane in place of alkoxychloromethane in the above process.

The compounds containing tetrahydrofuran-2'-yloxy, tetrahydropyran-2'-yloxy, or 4'-alkoxytetrahydropyran-4'-yloxy groups are preferably prepared from the corresponding hydroxy 2-naphthylacetic acid ester derivative by treatment with dihydrofuran, dihydropyran, or 4'-alkoxy dihydropyran, such as 4'-methoxy dihydropyran, in the presence of an acid catalyst.

The 4-alkoxy-2,6-dihydropyrans are prepared by treating 4-oxotetrahydropyran with an alkanol in the presence of an acid catalyst, and then pyrolyzing the resulting 4,4-dialkoxy tetrahydropyran in the presence of acid to afford the corresponding 4-alkoxy-2,6-dihydropyran.

The compounds containing hydroxy ester groups are prepared from the hydroxy derivatives by conventional esterification means, such as by heating with an acid anhydride.

The foregoing general procedures are useful for the preparation of the other naphthylacetic acid derivatives hereof.

Upon their preparation, the naphthylacetic acid derivatives can be converted to the corresponding amides, esters, and acid addition salts thereof via methods known per se as described above.

The following examples illustrate the manner by which this invention can be practiced and are not intended as limitations upon the overall scope hereof, but rather as illustrations of the present invention.

PREPARATION 1

Part A

A mixture of 12.2 g. of o-methoxy toluene, 20 g. of succinic anhydride, 27 g. of aluminum chloride, and 250 ml. of carbon disulfide is stirred for four hours; the mixture is poured into 500 g. of ice, and the products are isolated by extraction with benzene. The product, a mixture of 2-methoxy-4-(3'-carboxy-1'-oxopropyl)-toluene and 2-methoxy-5-(3'-carboxy-1'-oxopropyl)-toluene is reduced with sodium borohydride, hydrogenolyzed with hydrogen in the presence of palladium charcoal catalyst, cyclized by treatment with concentrated sulfuric acid according to the procedures described in Part A of Example 3 to afford the mixed product 6-methyl-7-methoxy-1-tetralone and 7-methyl-6-methoxy-1-tetralone. The products are separated by distillation and identified by nuclear magnetic resonance.

Part B

Ten grams of the above mixed products are hydrogenolyzed by treatment with 6 g. of sodium borohydride in ethanol at 25° C for six hours. The mixture is acidified with aqueous 1N hydrochloric acid and the products 6-methyl-7-methoxy-1-hydroxy-1,2, 3,4-tetrahydro-2-naphthalene and 6-methoxy-7-methyl-1-hydroxy-1, 2,3,4-tetrahydro-2-naphthalene are isolated by benzene extraction. The products are hydrogenolyzed and dehydrogenated according to the procedures described in Part B of Example 3 to give 2-methyl3-methoxynaphthalene.

Similarly, 6-chloro-8-ethoxy-4-tetralone and 6-ethoxy-8-chloro-4-tetralone are prepared from 1-chloro-3-ethoxybenzene. By means of the process described in Part B, 6-chloro-8-ethoxynaphthalene and 6-ethoxy-8-chloronaphthalene are prepared from the corresponding 1-tetralones. The products are separated by distillation and identified by nuclear magnetic resonance.

Part C

A mixture of 21 g. of 6-chloro-8-ethoxy tetralin (prepared from 6-chloro-8-ethoxy-4-tetralone by reducing and hydrogenolyzing the latter by the means described in Part B above), 30 g. of chromium trioxide and 500 ml. of glacial acetic acid is stirred for 24 hours at room temperature. The mixture is diluted with 500 ml. of aqueous ice-cold 10% sodium bisulfite, neutralized by the addition of aqueous 15% sodium hydroxide, and extracted with methylene chloride. The extracts are combined, washed with water, dried and evaporated to yield a mixture of 6-chloro-8-ethoxy-1-tetralone and 6-chloro-8-ethoxy-4-tetralone. The products are separated by distillation under reduced pressure.

Likewise, by means of the above process, 7-fluoro-1-tetralone is prepared from fluorobenzene, and β-fluoronaphthalene is prepared from 7-fluoro-1-tetralone by means of the process described in Part B.

Similarly, 7-methoxy-1-tetralone, 7-isopropyl-1-tetralone, 7-methylthio-1-tetralone, 6-chloro-7-methylthio-1-tetralone, 6-fluoro-7-methyl-1-tetralone, 6-methoxy-7-fluoro-1-tetralone, 6, 8-dimethyl-1-tetralone, 6-methylthio-8-cyclopropyl-1-tetralone, 6-methyl-8-isopropyl-1-tetralone, 2-methylthio-3-chloronaphthalene, 2-methyl-3-fluoronaphthalene, 2-fluoro-3-methoxynaphthalene, 1,3-dimethylnaphthalene, 1-methylthio-3-cyclopropylnaphthalene, and 1-isopropyl-3-methylnaphthalene are prepared from substituted benzene derivatives by means of the above processes.

PREPARATION 2

Part A

A mixture of 15.5 g. of 2-vinylnaphthalene, 23 g. of diiodomethane, 19.6 g. of zinc-copper couple (comprising 19.5 g. of zinc and 0.1 g. of copper) and 500 ml. of diethyl ether is refluxed for eight hours; the cooled mixture is then filtered, washed with dilute hydrochloric acid, washed with water to neutrality, dried and evaporated to yield 2-cyclopropylnaphthalene.

Part B

To a mixture of 23.1 g. of naphthyl magnesium bromide and 250 ml. of diethyl ether, 7 g. of cyclobutanone are slowly added. After the addition, the mixture is refluxed for one hour, cooled, acidified with aqueous hydrochloric acid and filtered. The product is isolated by methylene chloride extraction to furnish 2-(1'-hydroxycyclobutyl)-naphthalene. The product is hydrogenated in 200 ml. of ethanol with a molar equivalent of hydrogen in the presence of 50 g. of Raney nickel; the reaction mixture is filtered after the hydrogenation and evaporated to furnish 2-cyclobutylnaphthalene.

Part C

To a mixture of 15.5 g. of 2-vinylnaphthalene and 300 ml. of chloroform, a 5% bromine chloroform solution is added at −10° C until the bromine color persists. The mixture is then added to 200 ml. of ammonia containing 15 g. of sodium amide. The mixture is allowed to evaporate; the residue is extracted with diethyl ether. The extracts are combined, washed to neutrality with water, dried, and evaporated to yield 2-ethynylnaphthalene.

PREPARATION 3

A mixture of 14.6 g. of 2-tetralone, 20 g. of p-fluorophenyl magnesium bromide, and 200 ml. of diethyl ether is stirred for four hours and then refluxed for one hour. The mixture is acidified with the addition of 200 ml. of 1N hydrochloric acid, filtered, and extracted with diethyl ether. The extracts are combined, washed with water to neutrality, filtered, dried and evaporated. The residue, containing 2-p-fluorophenyl-3,4-dihydronaphthalene is mixed with 25 g. of 5% palladium-on-charcoal catalyst; the resulting mixture is heated to 200° C for 6 hours, cooled, diluted with 250 ml. of chloroform, filtered, and evaporated to give 2-p-fluorophenylnaphthalene.

Similarly, 2-p-chlorophenylnaphthalene and 2-p-tolylnaphthalene are prepared by using p-chlorophenyl magnesium bromide and p-tolyl magnesium bromide respectively in place of p-fluorophenyl magnesium bromide in the above process.

EXAMPLE 1

To a mixture of 1.6 g. of β-methoxynaphthalene, 1.6 g. of acetyl chloride, and 20 ml. of nitrobenzene, 4.0 g. of aluminum chloride are slowly added. The resulting mixture is stirred for 48 hours at 25° C; then it is washed with water until free of chloride. The mixture is dried over sodium sulfate and evaporated under reduced pressure. The residue, 2-acetyl-6-methoxynaphthalene, is refluxed in 2 ml. of morpholine containing one-half gram of sulfur for two hours; the reaction mixture is then filtered and evaporated. The resulting thio amide derivative is extracted with diethyl ether; the extracts are combined and evaporated. The residue is refluxed in 10 ml. of concentrated hydrochloric acid for two hours, cooled to 25° C, and made alkaline with aqueous sodium hydroxide. The mixture is then extracted with ether and the extracts discarded. The aqueous layer is acidified and the precipitated 6-methoxy-2-naphthylacetic acid filtered.

Similarly, 2-naphthylacetic acid, 6-chloro-2-naphthylacetic acid, 6-fluoro-2-naphthylacetic acid, 6-ethoxy-2-naphthylacetic acid, 6-ethylthio-2-naphthylacetic acid, 6-methylthio-2-naphthylacetic acid, 6-methyl-2-naphthylacetic acid, 6-ethyl-2-naphthylacetic acid, 6-isopropyl-2-naphthylacetic acid, 6-cyclopropyl-2-naphthylacetic acid, 6-cyclohexyl-2-naphthylacetic acid, 6-hydroxy-2-naphthylacetic acid, 6-vinyl-2-naphthylacetic acid, 6-ethynyl-2-naphthylacetic acid, 6-formyl-2-naphthylacetic acid, 6-carboxy-2-naphthylacetic acid, 6-methoxycarbonyl-2-naphthylacetic acid, 6-acetyl-2-naphthylacetic acid, 6-cyano-2-naphthylacetic acid, 6-phenyl-2-naphthylacetic acid, 6-p-chlorophenyl-2-naphthylacetic acid, 6-methyl-8-fluoro-2-naphthylacetic acid, 6-methyl-8-methoxy-2-naphthylacetic acid, 6-chloro-8-methyl2-naphthylacetic acid, 6,7-dichloro-2-naphthylacetic acid, 6-fluoro-7-methoxy-2-naphthylacetic acid, 6-methoxy-7-fluoro-2-naphthylacetic acid, 6,7-dimethyl-2-naphthylacetic acid, 6,8-dimethoxy-2-naphthylacetic acid, 6-methyl-8-fluoro-2-naphthylacetic acid, 6-chloro-8-methyl-2-naphthylacetic acid, 6-methyl-8-chloro-2-naphthylacetic acid are prepared from their respective corresponding naphthalene starting materials.

EXAMPLE 2

Part A

A mixture of 18 g. of 6-methoxy-1-tetralone, 60 g. of diethyl carbonate, 2.5 g. of sodium hydride, and 200 ml. of toluene is heated to 60° C for 5 hours. The mixture is cooled, acidified by the addition of 200 ml. of 1N hydrochloric acid, and then extracted with three 75 ml. portions of benzene. The extracts are combined, washed with water to neutrality, and dried over sodium sulfate. The mixture, containing 6-methoxy-2-ethoxycarbonyl-1-tetralone, is treated with 2.5 g. of sodium hydride at room temperature with stirring. Twenty grams of ethyl α-bromoacetate are then added and the mixture is allowed to stand for 12 hours at room temperature. The mixture is added to 500 ml. of water and extracted with methylene chloride. The extracts are combined, washed with water to neutrality, dried over sodium sulfate, and evaporated. The residue, containing 6-methoxy-2-ethoxycarbonyl2-(ethoxycarbonylmethyl)-1-tetralone, is refluxed in 200 ml. of 6N hydrochloric acid for 24 hours and then the reflux mixture is evaporated. The residue, containing 6-methoxy-2-(carboxymethyl)-1-tetralone, is reduced by treating it with 200 ml. of ethanol containing 8 g. of sodium borohydride. After one hour, the mixture is acidified with the addition of 100 ml. of 3N hydrochloric acid, and the resulting mixture is extracted with several portions of methylene chloride. The extracts are combined, washed with water to neutrality, dried over sodium sulfate, and evaporated. The residue, containing 6-methoxy-1-hydroxy-1,2,3,4-tetrahydro-2-naphthylacetic acid, is hydrogenolyzed by hydrogenating with one equivalent of hydrogen in acetic acid containing 300 mg. of 5% palladium-on-barium sulfate. The hydrogenation mixture is filtered and evaporated. The residue, containing 6-methoxy-1,2,3,4-tetrahydro-2-naphthylacetic acid, is dissolved in 200 ml. of diethyl ether and the mixture is then added to a 100 ml. solution of diethyl ether containing 4 g. of diazomethane. The mixture is then evaporated to dryness. The esterified residue is dehydrogenated by adding it to 1 g. of 10% palladium-on-charcoal and heating the resulting mixture for six hours at 200° C. The cooled mixture is diluted with 200 ml. of chloroform, filtered, and evaporated to afford methyl 6-methoxy-2-naphthylacetate.

Similarly, methyl 6-methyl-2-naphthylacetate, methyl-6-methylthio-2-naphthylacetate, and methyl 6-chloro-2-naphthylacetate are prepared from 6-methyl-1-tetralone, 6-methylthio-1-tetralone and 6-chloro-1-tetralone, respectively, by means of the above process.

By means of the above process, methyl 7-methyl-2-naphthylacetate, methyl 7-ethyl-2-naphthylacetate, methyl 7-isopropyl-2-naphthylacetate, methyl 7-fluoro-2-naphthylacetate, methyl 7-chloro-2-naphthylacetate, methyl 7-methylthio-2-naphthylacetate, methyl 7-methoxy-2-naphthylacetate, and methyl 7-propoxy2-naphthylacetate are prepared from 7-methyl-1-tetralone, 7-ethyl-1-tetralone, 7-isopropyl-1-tetralone, 7-fluoro-1-tetralone, 7-chloro-1-tetralone, 7-methoxy-1-tetralone, 7-methylthio-1-tetralone, and 7-hydroxy-1-tetralone, respectively.

Part B

A solution of 4.2 g. of diazomethane and 75 ml. of diethyl ether is added to a mixture of 23.6 g. of 6-methoxy-1-hydroxy-1,2,3,4-tetrahydro-2-naphthylacetic acid and 150 ml. of diethyl ether. The reaction mixture is stirred until colorless; then it is evaporated. The residue, containing methyl 6-methoxy1-hydroxy-1,2,3,4-tetrahydro-2-naphthylacetate is esterified by treatment with 240 mg. of sodium hydride in 25 ml. of methanol followed by the addition of 2.4 g. of methyl iodide. The product, methyl 1,6-dimethoxy-1,2,3,4-tetrahydro-2-naphthylacetate, is dehydrogenated by heating it with 2 g. of 10% palladium-on-charcoal catalyst; the resulting mixture is heated to 210° C for 12 hours. The cooled mixture is then diluted with 150 ml. of methylene chloride, filtered, and evaporated to yield methyl 1,6-dimethoxy-2-naphthylacetate. The product is refluxed in a mixture of 150 ml. of glacial acetic acid and 150 ml. of 48% hydrobromic acid for ten minutes. The product is extracted with methylene chloride. The extracts are combined, washed with water to neutrality, dried over sodium sulfate, filtered and evaporated to yield a mixture of methyl 1-hydroxy-6-methoxy-2-naphthylacetate and methyl 1-methoxy-6-hydroxy-2-naphthylacetate. The compounds are separated by distillation under reduced pressure and identified by nuclear magnetic spectroscopy.

Similarly, methyl 1-hydroxy-2-naphthylacetate, methyl 6-fluoro-1-hydroxy-2-naphthylacetate, methyl 6-chloro-1-hydroxy-2-naphthylacetate, methyl 6-methyl-1-hydroxy-2-naphthylacetate, methyl-6-cyclopropyl-1-hydroxy-2-naphthylacetate, methyl 1,6-dihydroxy-2-naphthylacetate, methyl 6-methylthio-1-hydroxy-2-naphthylacetate, and methyl 6-ethyl-1-hydroxy-2-naphthylacetate are prepared from the corresponding unsubstituted and 6-substituted 1-hydroxy-1,2,3,4-tetrahydro-2-naphthylacetic acid by means of the above process.

Part C

To a mixture of 10 g. of boron trifluoride and 100 g. of methanol, 23 g. of 6-methoxy-2-(carboxymethyl)-1-tetralone are added. The reaction mixture is stirred for one hour and then evaporated to dryness. The residue, containing 6-methoxy-2-(methoxycarbonylmethylene)-1-tetralone, is converted to the enol ether by treating with a mixture of 11 g. of trimethylorthoformate, 0.2 g. of p-toluenesulfonic acid and 200 ml. of benzene. The reaction mixture is allowed to stand for 24 hours; then it is washed with water to neutrality, dried over sodium sulfate, filtered, and evaporated. The residue, containing methyl 1,6-dimethoxy-3,4-dihydro-2-naphthylacetate, is refluxed in a mixture of 45 g. of 2,3-dichloro-5,6-dicyano-1,4-benzoquinone and 200 ml. of xylene for six hours; the mixture is then filtered and evaporated to dryness. The residue is taken up in 200 ml. of acetone; this mixture is chromatographed on alumina and evaporated to yield methyl 1,6-dimethoxy-2-naphthylacetate.

Similarly, methyl 1-methoxy-6-methyl-2-naphthylacetate, methyl 1-methoxy-6-ethyl-2-naphthylacetate, methyl 1-methoxy-6-fluoro-2-naphthylacetate, methyl 1-methoxy-2-naphthylacetate, methyl 1-methoxy-6-isopropyl-2-naphthylacetate, and methyl 1-methoxy-6-methylthio-2-naphthylacetate are prepared from the corresponding unsubstituted and 6-substituted 2-(carboxymethylene)-1-tetralones by means of the above process.

By substituting other trialkyl orthoformates for trimethyl orthoformate in the above process, the corresponding 1-alkoxy-6-substituted-2-naphthylacetic acid esters are prepared. By employing triethyl orthoformate in the above process, methyl 1-ethoxy-6-methoxy-2-naphthylacetate is furnished.

Part D

To a mixture of 12 g of methyl magnesium bromide and 200 ml. of diethyl ether, 25 g. of 6-methoxy-2-(methoxycarbonylmethylene)-1-tetralone are added. The alkylating mixture is refluxed for one hour after it has been allowed to stand for one hour; the mixture is made acidic to litmus by the addition of 1N methanolic HCl, filtered, and evaporated. The residue, containing methyl 1-methyl-6-methoxy-3,4-dihydro-2-naphthylacetate, is added to 1 g. of 10% palladium-on-charcoal and the resulting mixture is heated to 180° C for six hours. The mixture is cooled, diluted with 200 ml. of chloroform, filtered, and evaporated to yield methyl 1-methyl-6-methoxy-2-naphthylacetate.

Similarly, methyl 1-methyl-2-naphthylacetate, methyl 1-methyl-6-chloro-2-naphthylacetate, methyl 1-methyl-6-fluoro-2-naphthylacetate, methyl 1,6-dimethyl-2-naphthylacetate, methyl 1-methyl-6-methylthio-2-naphthylacetate, and methyl 1-methyl-6-ethoxy-2-naphthylacetate are prepared from the corresponding unsubstituted and 6-substituted 2-methoxycarbonylmethyl-1-tetralones by means of the above process:

By employing ethyl magnesium bromide, isopropyl magnesium bromide, and hexyl magnesium bromide with 2-(methoxycarbonylmethyl)-1-tetralone in the above process, the following are prepared: methyl 1-ethyl-2-naphthylacetate, methyl 1-isopropyl-2-naphthylacetate, and methyl 1-hexyl-2-naphthylacetate.

Part E

To a mixture of 25 g. of 6-methoxy-2-(methoxycarbonylmethyl)-1-tetralone and 150 ml. of benzene, 21 g. of phosphorus pentachloride are slowly added. After the addition, the chlorination mixture is allowed to stand for an additional 5 hours; then it is added to 500 g. of ice and extracted with xylene. The extracts, containing methyl 1-chloro-6-methoxy-3,4-dihydro2 naphthylacetate, are combined, washed with water to neutrality and dried over sodium sulfate; then 23 g. of 2,3-dichloro-5,6-dicyano-1,4-benzoquinone are added and the resulting mixture is refluxed for five hours. The dehydrogenation mixture is cooled, filtered, and evaporated. The residue is taken up in acetone and chromatographed on alumina and evaporated to yield methyl 1-chloro6-methoxy-2-naphthylacetate.

Similarly, methyl 1-chloro-2-naphthylacetate, methyl 1-chloro-6-methyl-2-naphthylacetate, methyl 1-chloro-6-isopropyl-2-naphthylacetate, methyl 1-chloro-6-hydroxy-2-naphthylacetate, methyl 1-chloro-6-fluoro-2-naphthylacetate, methyl 1,6-dichloro-2-naphthylacetate, methyl 1-chloro-6-ethylthio-2-naphthylacetate, and methyl 1-chloro-6-methylthio-2-naphthylacetate are prepared from the corresponding unsubstituted or 6-substituted 2-(methoxycarbonylmethyl)-1-tetralone by means of the above process.

Part F

A mixture of 25 g. of methyl 1,6-dimethoxy-2-naphthylacetate, 50 g. of 48% aqueous hydrobromic acid and 50 ml. of glacial acetic acid are refluxed for two hours. The mixture is cooled, neutralized with the cautious addition of aqueous 5% sodium carbonate, and extracted with methylene chloride. The extracts are combined, washed with water, dried over sodium sulfate, and evaporated to dryness. The residue, containing methyl 1,6-dihydroxy-2-naphthylacetate is thio-etherified by adding it to a mixture of 50 g. of methylmercaptan and 1 ml. of concentrated sulfuric acid; the mixture is heated to 180° C under pressure for 12 hours. The mixture is cooled, diluted with 150 ml. of benzene, washed with water to neutrality, dried over sodium sulfate, and evaporated. The residue is refluxed in 200 ml. of methanol containing 10 g. of sodium methoxide for one hour; the product is extracted with methylene chloride. The extracts are combined, washed, dried and evaporated to give methyl 1,6-dimethylthio-2-naphthylacetic acid.

Similarly, melthyl 1-methylthio-2-naphthylacetate, methyl 1-methylthio-6-methyl-2-naphthylacetate, methyl 1-methylthio-6-fluoro-2-naphthylacetate, and methyl 1-methylthio-6-chloro-2-naphtylacetate are prepared from the corresponding unsubstituted and 6-substituted methyl 1-methoxy-2-naphthylacetates by means of the above process.

By utilizing ethylmercaptan, isopropylmercaptan or pentylmercaptan with methyl 1-hydroxy-2-naphthylacetate in the above process, the following are prepared: methyl 1-ethylthio-2-naphthylacetate, methyl 1-isopropyl-2-naphthylacetate, or methyl 1-pentylthio-2-naphthylacetate.

By treating 25 g. of methyl 6-methoxy-1-hydroxy-2-naphthylacetate with 10 ml. of methylmercaptan as described above for the 1,6-dihydroxy compound, methyl 6-methoxy-1-methylthio-2-naphthylacetate is obtained.

Part G

A mixture of 25 g. of methyl 6-methoxy-1-hydroxy-1,2,3,4-tetrahydro-2-naphthylacetate, 38 g. of 1-diethylamino-1,1,2-trifluoro-2-chloroethane and 150 ml. of methylene chloride are allowed to stand for 24 hours. The fluorination reaction mixture is added to 250 ml. of water containing 12 g. of hydrogen chloride; the resulting mixture is separated and the methylene chloride phase is washed with water, dried over sodium sulfate, and evaporated to yield methyl 6-methoxy-1-fluoro-1,2,3,4-tetrahyro-2-naphthylacetate and 6-methoxy-1,2-dihydro-2-naphthylacetate. The mixture is separated on alumina eluting with acetone: diethyl ether (1:4) and the separated fractions are identified by ultraviolet spectroscopy. The fraction containing methyl 6-methoxy-1-fluoro-2-naphthylacetate is evaporated and the residue is refluxed with 23 g. of 2,3-dichloro-5,6-dicyano-1,4-benzoquinone and 500 ml. of xylene for six hours. The cooled mixture is filtered and chromatographed on alumina eluting with chloroform. The fraction containing the product is evaporated to yield methyl 6-methoxy-1-fluoro-2-naphthylacetate.

Similarly, methyl 1,6-difluoro-2-naphthylacetate, methyl 1-fluoro-6-chloro-2-naphthylacetate, methyl 1-fluoro-6-methyl-2-naphthylacetate, methyl 1-fluoro-6-ethyl-2-naphthylacetate, methyl 1-fluoro-2-naphthylacetate, and methyl 1-fluoro-6-methylthio-2-naphthylacetate are prepared from the corresponding unsubstituted and 6-substituted methyl 1-hydroxy-1,2,3,4-tetrahydro-2-naphthyl-acetates.

Part H

A mixture of 25 g. of methyl 1,6-dimethoxy-2-naphthylacetate, 15 g. of sodium carbonate, 200 ml. of methanol, and 25 ml. of water are allowed to stand for 24 hours. The reaction mixture is then acidified with 200 ml. of 2N hydrochloric acid and extracted with methylene chloride. The extracts are combined, washed with water, dried over sodium sulfate, and evaporated to yield 1,6-dimethoxy-2-naphthylacetic acid.

Likewise, the methyl 2-naphthylacetates prepared in the preceding parts are hydrolyzed to the corresponding 2-naphthylacetic acids.

EXAMPLE 3

Part A

To a mixture of 11 g. of chlorobenzene, 26 g. of aluminum chloride and 250 ml. of carbon disulfide are added 22 g. of dimethyl 3-chlorocarbonyl glutarate. The resulting mixture is poured into 500 ml. of ice water after it has been allowed to stand for two hours. The aqueous mixture is extracted with methylene chloride; the extracts are combined, washed to neutrality with water, dried over sodium sulfate, and evaporated to give dimethyl 3-(p-chlorobenzoyl)-glutarate. The latter compound is reduced and hydrogenolyzed by means of the procedures described in Part A of Example 2 to furnish dimethyl 3-(p-chlorobenzyl)-glutarate. The glutarate derivative and 200 ml. of concentrated hydrochloric acid is refluxed for three hours, and then diluted with 500 ml. of water and the product extracted with ether. The residue, containing 3-(p-chlorobenzyl)-glutaric acid, is taken up in 100 ml. of concentrated sulfuric acid and allowed to stand for one hour at room temperature; the reaction mixture is then diluted with a kilogram of ice and extracted with methylene chloride. The extracts are combined, washed with water, dried over sodium sulfate, and evaporated to yield 7-chloro-3-(carboxymethyl)-1-tetralone. The latter is esterified by adding it to a mixture of 10 g. of boron trifluoride etherate and 150 ml. of methanol. The resulting mixture is evaporated after being allowed to stand for four hours to furnish 7-chloro-3-(methoxycarbonylmethyl)-1-tetralone.

Similarly, 3-(methoxycarbonylmethyl)-1-tetralone, 7-methyl-3-(methoxycarbonylmethyl)-1-tetralone, 7-ethyl-3-(methoxycarbonylmethyl)-1-tetralone, 7-cyclopropyl-3-(methoxycarbonylmethyl)-1-tetralone, 7-isopropyl-3-(methoxycarbonylmethyl)-1-tetralone, 7-methylthio-3-(methoxycarbonylmethyl)-1-tetralone, 7-fluoro-3-(methoxycarbonylmethyl)-1-tetralone, 7-methoxy-3-(methoxycarbonylmethyl)-1-tetralone, 7-ethoxy-3-(methoxycarbonylmethyl)-1-tetralone, and 7-ethylthio-3-(methoxycarbonylmethyl)-1-tetralone are prepared from benzene, methylbenzene, ethylbenzene, cyclopropylbenzene, isopropylbenzene, methylthiobenzene, fluorobenzene, methoxybenzene, ethoxybenzene and methylthiobenzene, respectively, by means of the above process.

Part B

To a mixture of 8 g. of sodium borohydride and 150 ml. of methanol, 23.5 g. of 7-fluoro-3-(methoxycarbonylmethyl)-1-tetralone are added. The mixture is diluted with 250 ml. of 2N hydrochloric acid after standing for four hours at 25° C; the aqueous mixture is then extracted with chloroform. The extracts are combined, washed with water to neutrality, dried over sodium sulfate, filtered, and evaporated to yield methyl 6-fluoro-4-hydroxy-1,2,3,4-tetrahydro-2-naphthylacetate. The latter compound is dehydrogenated by the process described in Part B of Example 2 to furnish methyl 6-fluoro-4-hydroxy-2-naphthylacetate.

Similarly, the 1-tetralones, prepared by means of the process of Part A above, are treated as described above to afford the corresponding 4-hydroxy 2-naphthylacetic acid ester derivatives. Accordingly, methyl 6-methyl-4-hydroxy-1,2,3,4-tetrahydro-2-naphthylacetate and methyl 6-methyl-4-hydroxy-2-naphthylacetate are prepared from 7-methyl-3-(methoxycarbonylmethyl)-1-tetralone by means of the above described processes.

Part C

7-Methoxy-3-(methoxycarbonylmethyl)-1-tetralone is converted to the enol ether and dehydrogenated by means of the processes described in Part C of Example 2 to furnish methyl 4,6-dimethoxy-2-naphthylacetate.

Similarly, other methyl 4-alkoxy-2-naphthylacetates are prepared from the corresponding unsubstituted- or 7-substituted-3-(methoxycarbonylmethyl)-1-tetralones. Accordingly, methyl 4-methoxy-2-naphthylacetate is prepared from 3-(methoxycarbonylmethyl)-1-tetralone.

Part D

7-Methyl-3-(methoxycarbonylmethyl)-1-tetralone is alkylated and dehydrogenated by the processes described in Part D of Example 2 to afford methyl 4,6-dimethyl-2-naphthylacetate.

Similarly, other unsubstituted- or 7-substituted-3-(methoxycarbonylmethyl)-1-tetralones are alkylated and dehydrogenated to furnish the corresponding unsubstituted- or 6-substituted-methyl 4-alkyl-2-naphthylacetates. Thus, methyl 4-isopropyl-6-chloro-2-naphthylacetate is prepared from 7-chloro-3-(methoxycarbonylmethyl)-1-tetralone and isopropyl magnesium bromide.

Part E

7-Chloro-3-(methoxycarbonylmethyl)-1-tetralone is chlorinated and dehydrogenated by the procedures described in Part E of Example 2 to afford methyl 4,6-dichloro-2-naphthylacetate Similarly, other substituted or 6-substituted methyl 4-chloro-2-naphthylacetates are prepared from the corresponding unsubstituted or 7-substituted 3-(methoxycarbonylmethyl)-1-tetralone by means of the aforementioned procedures. Accordingly, methyl 4-chloro-6-methylthio-2-naphthylacetate is prepared from 7-methylthio-3-(methoxycarbonylmethyl)-1-tetralone.

Part F

Methyl 6-methoxy-2-naphthylacetate is thioetherified by the procedure described in Part F of Example 2 to afford methyl 4-methylthio-6-methoxy-2-naphthylacetate.

Similarly, methyl 4-methylthio-2-naphthylacetate, methyl 4-methylthio-6-methyl-2-naphthylacetate, methyl 4-methylthio-6-chloro-2-naphthylacetate, methyl 4-methylthio-6-fluoro-2-naphthylacetate, and methyl 4,6-dimethylthio-2-naphthylacetate are prepared from the corresponding unsubstituted and 6-substituted methyl 4-hydroxy-2-naphthylacetates by means of the above processes.

Part G

Methyl 6-methyl-4-hydroxy-1,2,3,4-tetrahydro-2-naphthylacetate is fluorinated and dehydrogenated by means of the procedures described in Part G of Example 2 to afford methyl 4-fluoro-6-methyl-2-naphthylacetate.

Similarly, other 4-hydroxy-1,2,3,4-tetrahydro compounds, prepared by means of the processes of Part B of this example, are fluorinated and dehydrogenated to afford the corresponding methyl 4-fluoronaphthylacetate derivative. Thus, methyl 6-methoxy-4-fluoro-2-naphthylacetate is prepared from methyl 6-methoxy-4-hydroxy-1,2,3,4-tetrahydro-2-naphthylacetate.

Part H

Methyl 1,6-dimethoxy-2-naphthylacetate is hydrolyzed by the means of the process described in Part H of Example 2 to furnish 1,6-dimethoxy-2-naphthylacetic acid.

Likewise, the other 2-naphthylacetic acid ester derivatives of this example are hydrolyzed to the corresponding 2-naphthylacetic acid derivatives.

EXAMPLE 4

Part A

To a mixture of 18 g. of methyl phenylacetate, 26 g. of aluminum chloride and 150 ml. of carbon disulfide, 20 g. of succinic anhydride are added. The reaction mixture is allowed to stand for two hours at 35°C; then it is added to a liter of ice water and extracted with methylene chloride. The extracts are combined, washed, dried, and evaporated to give methyl p-(3'-carboxy-1'-oxopropyl)-phenylacetate. This derivative is reduced with sodium borohydride and dehydroxylated with palladium charcoal catalyst by the procedures described in Part A of Example 2 to afford methyl p-(3'-carboxypropyl)-phenylacetate. This derivative is refluxed in 50 ml. of thionyl chloride for three hours and then it is evaporated. The residue, containing methyl p-(3'-chlorocarbonylpropyl)-phenylacetate, is taken up in ml. of benzene containing 40 g. of aluminum chloride, The resulting mixture is stirred for two hours at 20° C; then it is added to a liter of ice and water and extracted with methylene chloride. The extracts are combined, washed with water to neutrality, dried over sodium sulfate, and evaporated to give 7-(methoxycarbonylmethyl)-1-tetralone.

Part B

Methyl 8-hydroxy-2-naphthylacetate is prepared from 7-(methoxycarbonylmethyl)-1-tetralone by reducing the latter with an equivalent amount of sodium borohydride and dehydrogenating the resulting hydroxy derivative by heating with palladium charcoal catalyst by the processes described in Part A of Example 2.

Part C

Methyl 8-methoxy-2-naphthylacetate is prepared from 7-(methoxycarbonylmethyl)-1-tetralone by means of the esterification and dehydrogenation processes described in Part C of Example 2.

Part D

Methyl 8-methyl-2-naphthylacetate is prepared from 7-(methoxycarbonylmethyl)-1-tetralone by means of the alkylation and dehydrogenation procedure described in Part D of Example 2.

Similarly, methyl 8-ethyl-2-naphthylacetate and methyl 8-isopropyl-2-naphthylacetate are prepared from 7-(methoxycarbonylmethyl)-1-tetralone by utilizing ethyl magnesium bromide and isopropyl magnesium bromide, respectively, in the alkylation procedure.

Part E

By means of the chlorination and dehydrogenation procedures described in Part A of Example 2, methyl 8-chloro-2-naphthylacetate is prepared from 7-(methoxycarbonylmethyl)-1-tetralone.

Part F

Methyl 8-methylthio-2-naphthylacetate is prepared from methyl 8-hydroxy-2-naphthylacetate by means of the thioesterification process described in Part F of Example 2.

Part G

Methyl 8-hydroxy-1,2,3,4-tetrahydro-2-naphthylacetate (prepared from 7-(methoxycarbonylmethyl)-1-tetralone by means of the reduction process described in Part A of Example 2) is fluorinated and dehydrogenated by means of the processes described in Part G of Example 2 to afford methyl 8-fluoro-2-naphthylacetate.

Part H

8-Methoxy-2-naphthylacetic acid is prepared from methyl 8-methoxy-2-naphthylacetate by means of the hydrolysis procedure described in Part H of Example 2.

Similarly, the other ester derivatives prepared by the above procedures are hydrolyzed.

EXAMPLE 5

To a mixture of 22 g. of methyl 6-methyl-2-naphthylacetate, 2.5 g. of sodium hydride and 150 ml. of 1,2-dimethoxyethane, 25 g. of methyliodide are added. The reaction mixture is allowed to stand for several hours; then it is diluted with ethanol followed by water and extracted with methylene chloride. The extracts are combined, washed with water to neutrality, dried over sodium sulfate, filtered, and evaporated to yield methyl 6-methyl-2-naphthyl-α-methylacetate. This derivative is hydrolyzed by means of the process described in Part H of Example 2 to obtain 6-methyl-2-naphthyl-α-methylacetic acid.

6-Methyl-2-naphthyl-α-ethylacetic acid is prepared by using ethyliodide in place of methyliodide in the above process.

Similarly, 2-naphthyl-α-methylacetic acid, 1-methyl-2-naphthyl-α-methylacetic acid, 1-fluoro-2-naphthyl-α-methylacetic acid, 1-methoxy-2-naphthyl-α-methylacetic acid, 1,6-dimethylthio-2-naphthyl-α-methylacetic acid, 4-ethyl-2-naphthyl-α-ethylacetic acid, 4-chloro-2-naphthyl-α-methylacetic acid, 4-methoxy-2-naphthyl-α-methylacetic acid, 4-methyl-6-fluoro-2-naphthyl-α-methylacetic acid, 4-fluoro-6-methoxy-2-naphthyl-α-methylacetic acid, 6-ethoxy-2-naphthyl-α-methylacetic acid, 6-ethyl-2-naphthyl-α-methylacetic acid, 6-methoxymethyl-2-naphthyl-α-methylacetic acid, 6-trifluoro-2-naphthyl-α-methylacetic acid, 6-isopropyl-2-naphthyl-α-methylacetic acid, 6-vinyl-2-naphthyl-α-methylacetic acid, 6-cyclopropyl-2-naphthyl-α-methylacetic acid, 6-fluoro-2-naphthyl-α-methylacetic acid, 6-chloro-2-naphthyl-α-methylacetic acid, 6-chloro-2-naphthyl-α-ethylacetic acid, 6-acetyl-2-naphthyl-α-methylacetic acid, 6-methoxy-2-naphthyl-α-methylacetic acid, 6-methoxymethylene-2-naphthyl-α-methylacetic acid, 6-methylthio-2-naphthyl-α-methylacetic acid, 6-ethylthio-2-naphthyl-α-methylacetic acid, 6-fluoro-7-methyl-2-naphthyl-α-methylacetic acid, 6-methyl-7-methoxy-2-naphthyl-α-methylacetic acid, 6-methylthio-7-fluoro-2-naphthyl-α-methylacetic acid, 7-chloro-2-naphthyl-α-methylacetic acid, 7-methoxy-2-naphthyl-α-methylacetic acid, 7-methyl-2-naphthyl-α-methylacetic acid, 8-methyl-2-naphthyl-α-methylacetic acid, 8-ethoxy-2-naphthyl-α-methylacetic acid, 8-fluoro-2-naphthyl-α-methylacetic acid, 8-isopropylthio-2-naphthyl-α-methylacetic acid, 6,8-dimethyl-2-naphthyl-α-methylacetic acid, and 6,8-dichloro-8-methyl-2-naphthyl-α-methylacetic acid are prepared from the corresponding methyl 2-naphthylacetic derivatives.

EXAMPLE 6

To a mixture of 25.2 g. of methyl 6-vinyl-2-naphthyl-α-methylacetate and 300 ml. of chloroform, a 5% bromine chloroform solution is added at −10° C until the bromine color persists. The mixture is then added to 200 ml. of ammonia containing 15 g. of sodium amide. The mixture is allowed to evaporate; the residue is extracted with diethyl ether. The extracts are combined, washed to neutrality with water, dried, and evaporated to yield methyl 6-ethynyl-2-naphthyl-α-methylacetate.

Similarly, ethyl 6-ethynyl-2-naphthyl-α-difluoromethylacetate is prepared from ethyl 6-vinyl-2-naphthyl-α-difluoromethylacetate.

EXAMPLE 7

To a mixture of 23 g. of ethyl 6-methoxy-2-naphthylacetate, 7 g. of sodium metal wire, and 150 ml. of benzene, 15 g. of ethyl formate are added; the resulting mixture is stirred for 24 hours and then 100 ml. of ethanol are added. The reaction mixture is made acidic by the addition of 500 ml. of 1N hydrochloric acid and then extracted with benzene. The extracts are combined, washed with water to neutrality, dried over sodium sulfate, and filtered. The benzene solution, which contains ethyl 6-methoxy-2-naphthyl-α,α-hydroxymethylacetate, is treated with 2.4 g. of sodium hydride; the resulting mixture is then treated with 3.6 g. of chlorine and the reaction mixture is allowed to stand for two hours at 25° C and then evaporated. The residue, containing ethyl 6-methoxy-2-naphthyl-α-formyl-α-chloroacetate, is taken up in methylene chloride, washed with water to neutrality, dried, filtered, and evaporated. The residue is taken up in 95% acetic acid containing 20 g. of chromium trioxide and the resulting mixture allowed to stand for two hours; the mixture is then diluted with water and extracted with methylene chloride. The extracts are combined, washed to neutrality, dried, filtered, and evaporated. The residue, containing ethyl 6-methoxy-2-naphthyl-α-carboxy-α-chloroacetate, is heated to 50° C to afford ethyl 6-methoxy-2-naphthyl-α-chloroacetate.

By using 9.3 g. of perchloryl fluoride in place of chlorine in the above process, ethyl 6-methoxy-2-naphthyl-α-fluoroacetate is afforded.

Similarly, other 2-naphthylacetic acid ester derivatives are chlorinated or fluorinated in the α-position. Thus, methyl 2-naphthyl-α-chloroacetate and methyl 2-naphthyl-α-fluoroacetate are prepared from methyl 2-naphthylacetate by means of the above processes.

EXAMPLE 8

To a mixture of 30 g. of methyl 6,7-dichloro-2-naphthyl-α,α-hydroxymethyleneacetate (prepared via the procedure described in Example 6) and 150 ml. of benzene, 20 g. of phosphorus pentachloride are slowly added. The reaction mixture is stirred for four hours after the completion of the addition; then 100 ml. of pyridine are added followed by the addition of 500 ml. of water. The reaction mixture is filtered; the product is isolated from the filtrate by extraction with methylene chloride to yield methyl 6,7-dichloro-2-naphthyl-α,α-chloromethyleneacetate.

Similarly, methyl 6-methylthio-2-naphthyl-α,α-chloromethyleneacetate is prepared from methyl 6-methylthio-2-naphthyl-α,α-hydroxymethyleneacetate.

EXAMPLE 9

A mixture of 25 g. of methyl 6-methyl-2-naphthyl-α-chloroacetate, 10 g. of sodium hydroxide, and 200 ml. of ethanol is refluxed for two hours. The cooled mixture is acidified by the addition of 1N hydrochloric acid. The resulting product, methyl 6-methyl-2-naphthyl-α-hydroxyacetate, is isolated by extractions with methylene chloride. The product is oxidized by means of the oxidation procedure described in Example 6 to give methyl 6-methyl-2-naphthyl-α-oxoacetate. The latter product is refluxed with 31 g. of difluoromethylene triphenyl phosphorane (prepared by allowing sodium chlorodifluoroacetate to react with triphenyl phosphine in diethyl ether) in 150 ml. of benzene. The resulting mixture is distilled under vacuum. The distillate is evaporated to yield methyl 2-naphthyl-α,α-difluoromethyleneacetate.

Methyl 6-methyl-α,α-chlorofluoromethyleneacetate is prepared by using 33 g. of chlorofluoromethylene triphenyl phosphorane (prepared by allowing sodium dichlorofluoroacetate to react with triphenyl phosphine) in place of difluoromethylene triphenyl phosphorane.

Similarly, other 2-naphthyl-α,α-difluoromethyleneacetic acid ester derivatives and 2-naphthyl-α,α-chlorofluoromethyleneacetic acid ester derivatives are prepared from the corresponding 2-naphthyl-α-chloroacetate derivatives by means of the above described procedures. Accordingly, methyl 6-fluoro-7-methoxy-2-naphthyl-α,α-difluoromethyleneacetate and methyl 6-fluoro-7-methoxy-2-naphthyl-α,α-chlorofluoromethyleneacetate are prepared from methyl 6-fluoro-7-methoxy-2-naphthyl-α-chloroacetate.

EXAMPLE 10

A mixture of 22 g. of methyl 6-fluoro-2-naphthylacetate, 10 g. of sodium methoxide, 6 g. of paraformaldehyde, and 200 ml. of dimethylsulfoxide is stirred for 18 hours at 25° C; the reaction mixture is acidified by the addition of 250 ml. of 1N hydrochloric acid and extracted with methylene chloride. The extracts are combined, washed, dried, filtered, and evaporated to yield a mixture of methyl 6-fluoro-2-naphthyl-α,α-methyleneacetate and methyl 6-fluoro-2-naphthyl-α-hydroxymethylacetate. The two products are separated by chromatographing on alumina, eluting with methanol-diethyl ether; the fractions are identified by ultraviolet spectroscopy.

Similarly, other 2-naphthyl-α,α-methyleneacetic acid ester derivatives are prepared from the corresponding 2-naphthylacetic acid ester derivatives.

EXAMPLE 11

A mixture of 23 g. of methyl 6-methyl-2-naphthalene-α,α-methyleneacetate, 23 g. of diiodomethane, 19.6 g. of zinc-copper couple (comprising 19.5 g. of zinc and 0.1 g. of copper) and 500 ml. of diethyl ether is refluxed for 6 hours and then cooled and filtered. The filtrate is washed with 0.1N hydrochloric acid, washed with water to neutrality, dried, and evaporated to yield methyl 6-methyl-2-naphthyl-α,α-ethyleneacetate.

Similarly, other 2-naphthyl-α,α-ethyleneacetic acid ester derivatives are prepared from the corresponding 2naphthyl-α,α-methyleneacetic acid ester derivatives. Thus, methyl 6,7-dimethoxy-2-naphthyl-α,α-ethyleneacetate is prepared from methyl 6,7-dimethoxy-2-naphthyl-α,α-methyleneacetate.

EXAMPLE 12

Part A

A mixture of 24.4 g. of ethyl 6-methoxy-2-naphthylacetate, 2.4 g. of sodium hydride, and 100 ml. of diethyl carbonate is stirred for four hours at 20° C. The product, diethyl 6-methoxy-2-naphthylmalonate (isolated by methylene chloride extraction), is added to 125 ml. of 1,2-dimethoxyethane containing 33 g. of potassium tert-butoxide; the mixture is allowed to stand for 4 hours at 60° C with chlorodifluoromethane being continually bubbled in after the mixture is initially saturated. The mixture is carefully neutralized by the addition of aqueous oxalic acid; the product, diethyl 6-methoxy-2-naphthyl-α-difluoromethylacetate, is isolated by methylene chloride extraction and hydrolyzed by refluxing in 250 ml. of methanol containing 5 g. of potassium hydroxide and 5 ml. of water. The cooled mixture is acidified with oxalic acid and the product, 6-methoxy-2-naphthyl-α-difluoromethylmalonic acid, is extracted with methylene chloride. The dried product is decarboxylated by heating to 180° C for 6 hours to give 6-methoxy-2-naphthyl-α-difluoromethylacetic acid.

Similarly, the α-difluoromethyl derivatives of the following compounds are prepared from the corresponding esters: 1-ethyl-2-naphthylacetic acid, 1-chloro-2-naphthylacetic acid, 1-methylthio-2-naphthylacetic acid, 1,6-dimethyl-2-naphthylacetic acid, 4-isopropyl-2-naphthylacetic acid, 4-fluoro-2-naphthylacetic acid, 4-ethylthio-2-naphthylacetic acid, 4-methyl-6-methoxy-2-naphthylacetic acid, 4-methoxy-6-chloro-2-naphthylacetic acid, 6-methyl-2-naphthylacetic acid, 6-isopropyl-2-naphthylacetic acid, 6-cyclopropyl-2-naphthylacetic acid, 6-trifluoromethyl-2-naphthylacetic acid, 6-methoxy-2-naphthylacetic acid, 6-methylthio-2-naphthylacetic acid, 7-fluoro-2-naphthylacetic acid, 7-methylthio-2-naphthylacetic acid, 6,7-dimethyl-2-naphthylacetic acid, 6,7-dichloro-2-naphthylacetic acid, 6-methoxy-7-methyl-2-naphthylacetic acid, 8-ethyl-2-naphthylacetic acid, 8-chloro-2-naphthylacetic acid, 8-ethylthio-2-naphthylacetic acid, and 6,8-dimethoxy-2-naphthylacetic acid.

Part B

A mixture of 31.6 g. of diethyl 6-methoxy-2-naphthylmalonate, 2.4 g. of sodium hydride, and 350 ml. of methanol is stirred for one hour; then 24 g. of methyliodide are added and the resulting mixture is refluxed for two hours. The cooled mixture is neutralized with aqueous oxalic acid. The product, diethyl 6-methoxy-2-naphthyl-α-methylmalonate, is isolated, hydrolyzed, and decarboxylated by the means of the above described processes to give 6-methoxy-2-naphthyl-α-methylacetic acid.

EXAMPLE 13

A mixture of 24.4 g. of methyl 6-methoxy-2-naphthyl-α-methylacetate, 25 g. of sodium metal, and 500 ml. of anhydrous iso-amyl alcohol are refluxed for 18 hours. The cooled reaction mixture is acidified by the addition of aqueous 1N hydrochloric acid. The product is isolated by diethyl ether extraction to give methyl 6-methoxy-3,4-dihydro-2-naphthyl-α-methylacetate.

Similarly, methyl 1-methyl-3,4-dihydro-2-naphthylacetate, methyl 1-fluoro-3,4-dihydro-2-naphthylacetate, methyl 1-isopropoxy-3,4-dihydro-2-naphthylacetate, methyl 1,6-dimethoxy-3,4-dihydro-2-naphthyl-α-methylacetate, methyl 1-ethyl-3,4-dihydro-2-naphthylacetate, methyl 7-chloro-3,4-dihydro-2-naphthyl-α-methylacetate, methyl 7-methylthio-6-fluoro-3,4-dihydro-2-naphthylacetate, methyl 6,7-dimethoxy-3,4-dihydro-2-naphthyl-α-ethylacetate, methyl 6-methyl-3,4-dihydro-2-naphthyl-α-methylacetate, methyl 6-fluoro-3,4-dihydro-2-naphthyl-α-methylacetate,
methyl 6-isopropyl-3,4-dihydro-2-naphthyl-α-methylacetate, methyl 6-chloro-3,4-dihydro-2-naphthyl-α-methylacetate, methyl 6-methylthio-3,4-dihydro-2-naphthyl-α-methylacetate, methyl 6-trifluoromethyl-3,4-dihydro-2-naphthyl-α-methylacetate, methyl 6-difluoromethoxy-3,4-dihydro-2-naphthyl-α-methylacetate, methyl 6-methoxy-3,4-dihydro-2-naphthyl-α-methylacetate, methyl 6-methoxymethyloxy-3,4-dihydro-2-naphthyl-α-difluoromethylacetate, methyl 6-methylthio-3,4-dihydro-2-naphthylacetate, methyl 7-methoxymethylthio-3,4-dihydro-2-naphthylacetate,
methyl 7-isopropyl-3,4-dihydro-2-naphthyl-α-methylacetate, methyl 7-trifluoromethyl-3,4-dihydro-2-naphthylacetate, methyl 7-ethoxy-3,4-dihydro-2-naphthyl-α-methylacetate, methyl 6,7-dimethyl-3,4-dihydro-2-naphthyl-α-ethylacetate, methyl 6-fluoro-7-chloro-3,4-dihydro-2-naphthyl-α-methylacetate,
methyl 6-methoxy-7-fluoro-3,4-dihydro-2-naphthylacetate, methyl 8-methyl-3,4-dihydro-2-naphthyl-α-methylacetate, methyl 8-methoxy-3,4-dihydro-2-naphthyl-α-methylacetate, methyl 6,8-difluoro-3,4-dihydro-2-naphthylacetate, and methyl 6-methyl-8-methylthio-3,4-dihydro-2-naphthylacetate are prepared from the corresponding 2-naphthylacetic acid ester derivatives by means of the above process.

EXAMPLE 14

Part A

A mixture of 26 g. of methyl 6-methylthio-2-naphthyl-α-methylacetate, 200 ml. of glacial acetic acid, and 2 ml. of 48% hydrobromic acid are refluxed for 2 hours. The mixture is diluted with one liter of water and extracted with methyl chloride. The extracts are combined, washed with water, dried over sodium sulfate, filtered, and evaporated to yield 6-methyl-6-thio-2-naphthyl-α-methylacetic acid.

Part B

The above product is added to a mixture of 150 ml. of dioxane and 150 ml. of aqueous 20% sodium hydroxide. The resulting mixture is heated to 65° C and saturated with chlorodifluoromethane. The resulting mixture is allowed to stand for two hours while continuously bubbling in chlorodifluoromethane. The cooled reaction mixture is then acidified by the addition of aqueous 1N hydrochloric acid and extracted with diethyl ether. The extracts are combined, washed with water to neutrality, dried over sodium sulfate, filtered, and evaporated to yield methyl 6-difluoromethylthio-2-naphthyl-α-methylacetate.

Similarly, methyl 1-difluoromethoxy-2-naphthylacetate, methyl 8-difluoromethoxy-2-naphthylacetate, methyl 6-difluoromethoxy-2-naphthylacetate, methyl 6-difluoromethoxy-3,4-dihydro-2-naphthylacetate,
methyl 7-difluoromethylthio-2-naphthylacetate,
methyl 6-difluoromethylthio-2-naphthylacetate, methyl 4-difluoromethylthio-2-naphthylacetate, methyl 6,7-bis(difluoromethoxy)-2-naphthylacetate, methyl 6-difluoromethoxy-2-naphthyl-α-methylacetate, methyl 7-difluoromethoxy-2-naphthyl-α-methylacetate, methyl 1-difluoromethoxy-6-difluromethylthio-2-naphthyl-α-methylacetate, methyl 6-difluromethoxy-8-chloro-2-naphthyl-α-difluoromethylacetate, methyl 4-difluoromethylthio-6-methoxy-2-naphthyl-α,α-methyleneacetate, methyl 8-difluoromethoxy-3,4-dihydro-2-naphthyl-α,α-difluoromethyleneacetate, methyl 6-difluoromethylthio-1-methoxy-2-naphthyl-α-ethylacetate are prepared from the corresponding α-2-naphthylacetic acid ester derivatives by means of the above process.

EXAMPLE 15

A mixture of 23 g. of methyl 6-hydroxy-2-naphthyl-α-methylacetate, 25 g. of chlorodimethyl ether, and 500 ml. of dimethylformamide is allowed to stand at room temperature for 12 hours. The reaction mixture is evaporated under reduced pressure to give methyl 6-methoxymethyloxy-2-naphthyl-α-methylacetate.

Methyl 6-isopropoxymethyloxy-2-naphthyl-α-methylacetate and methyl 6-methylthiomethyloxy-2-naphthyl-α-methylacetate are similarly prepared by utilizing chloromethyl isopropyl ether and methylthio chloromethane, respectively, in place of chlorodimethyl ether in the above process.

Methyl 6-methoxymethylthio-2-naphthyl-α-methylacetate is prepared by utilizing methyl 6-thio-2-naphthyl-α-methylacetate in the above process. Likewise, methyl 6-methylthiomethylthio is prepared by using methyl 6-thio-2-naphthyl-α-methylacetate and methylthio chloromethane in the process described above.

Likewise, methyl 1-methoxymethyloxy 2-naphthlacetate, methyl 4,6-di(methoxymethyloxy)-2-naphthyl-α-methylacetate, methyl 1-methoxy-6-methoxymethyloxy-2-naphthyl-α,α-methyleneacetate, methyl 6,7-di(methoxymethylthio)-2-naphthyl-α-methylacetate, methyl 8-ethoxymethylthio-3,4-dihydro-2-naphthylacetate, methyl 4-ethoxymethyloxy-3,4-dihydro-2-naphthyl-α,α-difluoromethyleneacetate, methyl 6-methoxymethyloxy-3,4-dihydro-2-naphthyl-α-methylacetate, and methyl 7-methoxymethyloxy-2-naphthyl-α-difluoromethylacetate are prepared from the corresponding 2-naphthylacetic acid derivatives by means of the above process.

EXAMPLE 16

Part A

A mixture of 500 ml. of benzene and 25 g. of 4-methoxy-2,6-dihydropyran is dried by distilling off 50 ml. To the remaining cooled mixture, 2 g. of para-toluene sulfonyl chloride and 26.6 g. of methyl 6-hydroxy-2-naphthyl-α-difluoromethylacetate are added; the resulting mixture is stirred for 24 hours at 25° C. The mixture is neutralized by the addition of aqueous 5% sodium bicarbonate. The resulting mixture is extracted with methylacetate. The extracts are combined, washed with water, dried over sodium sulfate, filtered, and evaporated to give methyl 6-(4'-methoxytetrahydropyran-4'-yloxy)-2-naphthyl-α-difluoromethylacetate.

Similarly, methyl 6-tetrahydropyran-2'-yloxy-2-naphthyl-α-difluoromethylacetate is prepared by using dihydropyran in place of 4-methyloxydihydropyran in the above process.

Part B

A mixture of 22.8 g. of methyl 4-hydroxy-2-naphthyl-α,α-methyleneacetate, 100 g. of tetrahydrofuran-2'-yl benzoate, and 500 ml. of benzene are refluxed for 24 hours. The reaction mixture is distilled and the highest boiling fraction is collected to give methyl 4-tetrahydrofuran-2'-yloxy-2-naphthyl-α,α-methyleneacetate.

Similarly, methyl 6,8-bistetrahydrofuran-2'-yloxy-2-naphthyl-α-fluoroacetate is prepared from methyl 6,8-dihydro-2-naphthyl-α-fluoroacetate.

EXAMPLE 17

Chlorine gas is bubbled through a mixture of 23 g. of methyl 6-methyl-2-naphthyl-α-methylacetate and 1 g. of phosphorus pentachloride in 200 ml. of carbon tetrachloride in the presence of light until 21.3 g. of chlorine have been taken up. The reaction mixture is diluted with 200 ml. of pyridine, filtered, further diluted with 500 ml. of ether, washed with water to neutrality, dried over sodium sulfate, and evaporated to yield methyl 6-trichloromethyl-2-naphthyl-α-methylacetate. The above product is then refluxed in a mixture of 500 ml. of chlorobenzene and 17.9 g. of antimonytrifluoride. The cooled reaction mixture is washed with water, dried over sodium sulfate, and evaporated to yield methyl 6-trifluoromethyl-2-naphthyl-α-methylacetate.

Similarly, methyl 8-trifluoromethyl-2-naphthylacetate, methyl 1-methoxy-6-trifluoromethyl-2-naphthyl-α-ethylacetate, methyl 6-trifluoromethyl-2-naphthylacetate, methyl 6-trifluoromethyl-2-naphthyl-α,α-methyleneacetate, methyl 4-fluoro-6-trifluoromethyl-2-naphthyl-α,α-methyleneacetate, methyl 7-trifluoromethyl-2-naphthyl-α-methylacetate, methyl 4,6-trifluoromethyl-2-naphthylacetate, methyl 1-trifluoromethyl-3,4-dihydro-2-naphthyl-α-methylacetate, and methyl 6-trifluoromethyl-2-naphthyl-α-difluoromethylacetate are prepared from the corresponding methyl substituted 2-naphthylacetic acid ester derivatives by means of the above process.

EXAMPLE 18

Part A

A mixture of 24.2 g. of methyl 6-ethyl-2-naphthyl-α-methylacetate, 17.8 g. of N-bromosuccinimide, and 10 mg. of benzoylperoxide, and 300 ml. of chloroform are refluxed for two hours in the presence of light. The mixture is filtered and evaporated. The residue is heated in 200 ml. of glacial acetic acid containing 16 g. of sodium acetate at 60° C for 24 hours. Five hundred milliliters of water are added to the resulting mixture and the product is extracted by diethyl ether extractions. The product, methyl 6-(α-acetoxyethyl)-2-naphthyl-α-methylacetate, is hydrolyzed by adding it to a 5% aqueous sodium carbonate solution. The product, 6-(α-hydroxyethyl)-2-naphthyl-α-methylacetate, is isolated by diethyl ether extractions. The isolated product is oxidized by adding it to 200 ml. of glacial acetic acid containing 25 g. of chromium trioxide. The resulting mixture is allowed to stand at room temperature for 1 hour. Two hundred milliliters of a 10% sodium bisulfite solution are added and the mixture is extracted with diethyl ether. The extracts are combined, washed with water to neutrality, dried over sodium sulfate, filtered, and evaporated to give 6-acetyl-2-naphthyl-α-methylacetic acid.

Part B

To a mixture of 24 g. of 6-acetyl-2-naphthyl-α-methylacetic acid and 200 ml. of diethyl ether are added 4.2 g. of diazomethane in 100 ml. of diethyl ether. The resulting mixture is evaporated to give methyl 6-acetyl-2-naphthyl-α-methylacetate. The product is added to 200 ml. of aqueous 20% sodium hypochlorite. The resulting mixture is allowed to stand for 4 hours at room temperature. The mixture is acidified by the addition of aqueous 1N hydrochloric acid and extracted with diethyl ether. The extracts are combined, washed with water to neutrality, dried over sodium sulfate, filtered, and evaporated to give 6-carboxy-2-naphthyl-α-methylacetic acid.

Part C

The above product is etherified with 8.4 g. of diazomethane by the procedure described in Part B above to give methyl 6-methoxycarbonyl-2-naphthyl-α-methylacetate. The diester is hydrolyzed by refluxing in 200 ml. of ethyl alcohol containing 4 g. (one molar equivalent) of sodium hydroxide for 5 hours. The cooled mixture is acidified by the addition of aqueous 1N hydrochloric acid and the product is isolated by methylenechloride extraction to give 6-methoxycarbonyl-2-naphthyl-α-methylacetic acid.

Part D

A mixture of 25.8 g. of 6-methoxycarbonyl-2-naphthyl-α-methylacetic acid, 4 g. of sodium hydroxide, 10 ml. of water, and 500 ml. of methanol are heated to 50° C, cooled, and evaporated. The residue is taken up in 500 ml. of diethylene glycol dimethyl ether and diborane is bubbled through. The resulting mixture is saturated with diborane and then is allowed to stand for 18 hours. The reaction mixture is acidified by the addition of aqueous 1N hydrochloric acid. The mixture is extracted with methylene chloride. The extracts are combined, washed with water to neutrality, dried over sodium sulfate, filtered, and evaporated to give 6-hydroxymethyl-2-naphthyl-α-methylacetic acid.

Part E

A mixture of 23 g. of 6-hydroxymethyl-2-naphthyl-α-methylacetic acid, 230 g. of manganese dioxide, and 2 l. of chloroform are stirred for 12 hours; the mixture is filtered and evaporated to give 6-formyl-2-naphthyl-α-methylacetic acid.

Part F

A mixture of 22.8 g. of 6-formyl-2-naphthyl-α-methylacetic acid, 14 g. of hydroxylamine hydrochloride, 25 g. of sodium acetate, and 1 l. of ethyl alcohol are refluxed for one hour; the cooled reaction mixture is diluted with 1 l. of water and extracted with methylene chloride. The extracts are combined, washed with water to neutrality, dried over sodium sulfate, filtered, and evaporated to give the oxime of 6-formyl-2-naphthyl-α-methylacetic acid. The above oxime is refluxed in 1 l. of acetic anhydride containing 20 g. of p-toluenesulfonic acid for one hour; the reaction mixture is then evaporated to dryness. The residue is taken up in methylene chloride, washed with water, dried over sodium sulfate, filtered, and evaporated to yield 6-cyano-2-naphthyl-α-methylacetic acid.

Similarly, by means of the above processes, 6-acetyl-2-naphthyl-α-difluoromethylacetic acid, 6-carboxy-2-naphthyl-α-difluoromethylacetic acid, 6-methoxycarbonyl-2-naphthyl-α-difluoromethylacetic acid, 6-hydroxymethyl-2-naphthyl-α-difluoromethylacetic acid, 6-formyl-2-naphthyl-α-difluoromethylacetic acid, and the oxime thereof, and 6-cyano-2-naphthyl-α-difluoromethylacetic acid are prepared from methyl 6-ethyl-2-naphthyl-α-difluoromethylacetate.

By utilizing diazoethane or 2-diazopropane in place of diazomethane in the process of Part C, 6-ethoxycarbonyl-2-napthyl-α-methylacetic acid or 6-isopropylcarbonyl-2-naphthyl-α-methylacetic acid are obtained.

Part G

A mixture of 5 g. of 6-carboxy-2-naphthyl-α-methylacetic acid, 2 ml. of concentrated hydrochloric acid, and 250 ml. of methanol are refluxed for 10 minutes. The cooled mixture is evaporated to yield a mixture of 6-methoxycarbonyl-2-naphthyl-α-methylacetic acid, methyl 6-carboxy-2-naphthyl-α-methylacetate, and methyl 6-methoxycarbonyl-2-naphthyl-α-methylacetate. The mixture is separated by distillation and chromatography on alumina eluting with ether. The separated products are identified by nuclear magnetic resonance spectroscopy.

Part H

To a mixture of 24.4 g. of methyl 6-hydroxymethyl-2-naphthyl-α-methylacetate (prepared from 6-hydroxymethyl-2-naphthyl-α-methylacetic acid by esterifying the latter by means of the procedure described in Part A of this example) and 500 ml. of benzene are added 2.4 g. of sodium hydride. The resulting mixture is stirred for two hours; then 12.2 g. of methyliodide are added. The resulting mixture is next neutralized by the addition of aqueous 1N hydrochloric acid after it has been allowed to stand for one hour; the mixture is then washed with water, dried over sodium sulfate, and evaporated to give methyl 6-methoxymethyl-2-naphthyl-α-methylacetate.

Methyl 6ethoxymethyl-2-naphthyl-α-methylacetate is prepared by using 13.7 g. of ethyliodide in place of methyliodide in the above process.

EXAMPLE 19

To a mixture of 20 g. of sodium hydroxide and 400 ml. of methanol are added 24.5 g. of methyl 6-methoxy-2-naphthyl-α-methylacetate. The resulting reaction mixture is heated to 60° C for five hours. The cooled mixture is neutralized by the addition of aqueous 1N hydrochloric acid and extracted with methylene chloride. The extracts are combined, washed with water to neutrality, dried over sodium sulfate, filtered, and evaporated to give 6-methoxy-2-naphthyl-α-methylacetic acid.

Similarly, the other 2-naphthylacetic acid ester derivatives prepared by means of the procedures described in the other examples herein are hydrolyzed to the corresponding 2-naphthylacetic acid derivatives.

EXAMPLE 20

A suspension of 2.4 g. of sodium hydride and 50 ml. of benzene is added to a mixture of 23 g. of 6-fluoro-2-naphthyl-α-methylacetic acid and 450 ml. of benzene. The resulting mixture is stirred for four hours. The mixture is cooled to 0° C and 19 g. of oxalyl chloride are added; after the addition, the mixture is allowed to stand for 4 hours. The resulting mixture is then saturated with ammonia and allowed to stand for 8 hours.

This mixture is then evaporated under reduced pressure. The residue is taken up in methylene chloride, washed with water to neutrality, dried, filtered, and evaporated to give 6-fluoro-2-naphthyl-α-methylacetamide.

Similarly, N-methyl-6-fluoro-2-naphthyl-α-methylacetamide, N,N-dimethyl-6-fluoro-2-naphthyl-α-methylacetamide, N-ethyl-6-fluoro-2-naphthyl-α-methylacetamide, N,N-diethyl-6-fluoro-2-naphthyl-α-methylacetamide, 6-fluoro-2-naphthyl-α-methyl N-acetyl pyrrolidine, 6-fluoro-2-naphthyl-α-methyl N-acetyl piperidine, 6-fluoro-2-naphthyl-α-methyl N-acetyl morpholine, 6-fluoro-2-naphthyl-α-methyl N-acetyl piperazine, 6-fluoro-2-naphthyl-α-methyl N-acetyl-4'-methylpiperazine are prepared by means of the above process by replacing ammonia with methylamine, dimethylamine, ethylamine, diethylamine, pyrrolidine, piperidine, morpholine, piperazine, and 1-ethylpiperazine, respectively.

By means of the above process, the corresponding amides of the other 2-naphthylacetic acid derivatives made by means described herein are prepared. Accordingly, 6-methyl-2-naphthylacetamide is prepared from 6-methyl-2-naphthylacetic acid.

EXAMPLE 21

To a solution of 26 g. of 6-methoxymethyloxy-2-naphthyl-α-methylacetic acid and 500 ml. of diethyl ether are slowly added a solution comprising of 5.6 g. of diazoethane and 50 ml. of diethyl ether. The reaction mixture is allowed to stand for 15 minutes and then is evaporated under reduced pressure to yield ethyl 6-methoxymethyloxy-2-naphthyl-α-methylacetate. By replacing diazoethane with diazopropane in the above process, propyl 6-methoxymethyloxy-2-naphthyl-α-methylacetate is obtained.

By means of the above described process, the other 2-naphthylacetic acid derivatives made by the procedures described in the examples herein are esterified.

EXAMPLE 22

A mixture of 32 g. of methyl 6-difluoromethoxy-2-naphthyl-α-difluoromethylacetate, 10 g. of sodium methoxide, 14 g. of hydroxylamine hydrochloride, and 500 ml. of methanol are allowed to stand for 16 hours. The mixture is then filtered and evaporated. The residue is neutralized by the addition of aqueous 1N hydrochloric acid and extracted by ether. The ether solution is then washed with water, dried, and evaporated to afford 6-difluoromethoxy-2-naphthyl-α-difluoromethyl acetohydroxamic acid.

Similarly, 6-methyl-2-naphthyl-α-methyl acethydroxamic is made by means of the above process from methyl 6-methyl-2-naphthyl-α-methyl acid.

Similarly, the corresponding hydroxamic acids of the other 2-naphthylacetic acid derivatives prepared via the procedures described in the examples herein are made by means of the above described process.

EXAMPLE 23

To a mixture of 4 g. of sodium hydroxide and 500 ml. of methanol are added 24.6 g. of 6-methylthio-2-naphthyl-α-methylacetic acid. The mixture is stirred for 18 hours at 50° C. The cooled mixture is then evaporated to give sodium 6-methylthio-2-naphthyl-α-methylacetate.

By employing potassium hydroxide, diethylamine, lysine, caffeine, or procaine in place of sodium hydroxide in the above process, the potassium triethylamine, lysine, caffeine, or procaine salt of 6-methylthio-2-naphthyl-α-methylacetic acid is obtained.

By means of the above procedure, the addition salts of the other 2-naphthylacetic acid derivatives made via the procedures described herein are prepared.

EXAMPLE 24

A mixture of 2.2 g. of 6-hydroxy-2-naphthyl-α-methylacetic acid, 50 ml. of acetic anhydride, and 100 mg. of p-toluenesulfonic acid is stirred for four hours at 50° C. The mixture is evaporated, water is added, and the mixture is extracted with diethyl ether which is washed with water to neutrality, dried over sodium sulfate, and evaporated to yield 6-acetoxy-2-naphthyl-α-methylacetic acid.

Methyl 6-acetoxy-2-naphthyl-α-methylacetate is prepared from the above product by means of the esterification procedure described in Example 21.

EXAMPLE 25

A mixture of 2.3 g. of 6-methoxy-2-naphthyl-α-methylacetic acid, 2.9 g. of cinchonidine, and 50 ml. of methanol is stirred for 2 hours; the mixture is then allowed to stand until crystallization is complete. The crystals are filtered off and washed with methanol. The crystals are recrystallized from methanol, filtered, washed, and dried. The pure crystals are added to 60 ml. of 0.2N hydrochloric acid. The resulting mixture is stirred for two hours and then extracted with diethyl ether. The extracts are combined, washed with water to neutrality, dried over sodium sulfate, and evaporated to yield one of the optical isomers of 6-methoxy-2-naphthyl-α-methylacetic acid. The filtrates from the above filtrations are acidified with aqueous dilute hydrochloric acid and the product is isolated by diethyl ether extractions to give the other optical isomer of 6-methoxy-2-naphthyl-α-methylacetic acid.

Similarly, the optical isomers of the other α-monosubstituted 2-naphthylacetic acid derivatives made via the procedures described herein are separated.

EXAMPLE 26

| Ingredients | Quantity per tablet, mgs. |
| --- | --- |
| 2-naphthylacetic acid | 50 |
| cornstarch | 200 |

The above ingredients are thoroughly mixed and pressed into single scored tablets, one tablet being administered every 3 to 4 hours.

EXAMPLE 27

| Ingredients | Quantity per tablet, mgs. |
| --- | --- |
| 6-methoxy-2-naphthyl-α-methylacetic acid | 30 |
| cornstarch | 100 |
| lactose | 370 |
| Magnesium stearate | 2 |

The above ingredients are mixed intimately and pressed into single scored tablets.

EXAMPLE 28

| Ingredients | Quantity per capsule, mgs. |
| --- | --- |
| 6-methylthio-2-naphth-yl-α-methylacetic acid | 25 |
| lactose | 225 |

The above ingredients are mixed and introduced into a No. 1 hard-shell gelatin capsule.

In a similar manner as that described in each of the preceding three examples, the following compounds can also be so formulated: 6-methoxy-2-naphthyl-α-methylacetic acid, 6-methylthio-2-naphthyl-α-methylacetic acid, 6-chloro-2-naphthyl-α-methylacetic acid, 6-fluoro-2-naphthyl-α-methylacetic acid, 6-methyl-2-naphthyl-α-methylacetic acid, 6-trifluoromethyl-2-naphthyl-α-methylacetic acid, 6-difluoromethoxy-2-naphthyl-α-methylacetic acid, 6-chloro-2-naphthylacetic acid, 6-methylthio-2-naphthylacetic acid, 6-methyl-2-naphthylacetic acid, 4-chloro-2-naphthylacetic acid, 3,4-dihydro-6-methoxy-2-naphthyl-α-methylacetic acid, 3,4-dihydro-6-methylthio-2-naphthyl-α-methylacetic acid, 3,4-dihydro-6-chloro-2-naphthyl-α-methylacetic acid, 1-methyl-2-naphthyl-α,α-methyleneacetic acid, sodium 8-chloro-2-naphthyl-α-fluoroacetate, methyl 6,7-dimethylthio-2-naphthylacetate, 4-methylthiomethyleneoxy-2-naphthyl-α-difluoromethylacetic acid, 4-methyl-2-naphthylacetic acid, 1-methoxy-6-(4'-methoxytetrahydropyran-4'-yloxy)-2-naphthylacetamide, potassium 3,4-dihydro-7-methyl-2-naphthyl-α,α-difluoromethyleneacetate, 3,4-dihydro-6-fluoro-2-naphthyl-α-methylacetic acid, 3,4-dihydro-6-methyl-2-naphthyl-α-methylacetic acid, 3,4-dihydro-6-difluoromethoxy-2-naphthyl-α-methylacetic acid, 3,4-dihydro-6-methoxy-2-naphthylacetic acid, 3,4-dihydro-6-methylthio-2-naphthylacetic acid, 3,4-dihydro-6-chloro-2-naphthylacetic acid, 3,4-dihydro-6-methyl-2-naphthylacetic acid, N,N-diethyl 4-isopropyl-2-naphthyl-α-methylacetamide, and the like.

What is claimed is:

1. A composition for treating inflammation, pain, pyrexia and pruritus in mammals which comprises a pharmaceutically acceptable non-toxic excipient and a therapeutically effective amount of a compound represented by the formula:

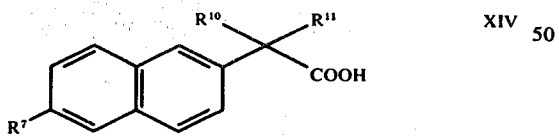

where:
$R^7$ is alkyl having 1 to 6 carbon atoms, cycloalkyl having 3 to 7 carbon atoms, hydroxymethyl, alkoxymethyl having 2 to 7 carbon atoms, trifluoromethyl, vinyl, ethynyl, fluoro, chloro, hydroxy or a conventional hydrolyzable ester thereof derived from a hydrocarbon carboxylic acid having 1 to 12 carbon atoms, alkoxy having 1 to 6 carbon atoms, difluoromethoxy, alkoxymethyloxy, having 2 to 7 carbon atoms, alkylthiomethyloxy having 2 to 7 carbon atoms, alkylthio having 1 to 6 carbon atoms, difluoromethylthio, alkoxymethylthio having 2 to 7 carbon atoms, alkylthiomethylthio having 2 to 7 carbon atoms, formyl, carboxy, alkoxycarbonyl having 2 to 7 carbon atoms, acetyl, cyano or phenyl optionally p-monosubstituted with methyl, fluoro, chloro, hydroxy, methoxy or ethyl; one of $R^{10}$ and $R^{11}$ is hydrogen, and the other is methyl, ethyl, difluoromethyl, fluoro or chloro, or $R^{10}$ and $R^{11}$ taken together are alkylidene, halomethylene or ethylene;
an alkyl ester of a compound of formula XIV derived from an alkanol having 1 to 12 carbon atoms; or a pharmaceutically acceptable addition salt thereof.

2. The composition according to claim 1 wherein said compound is 6-methoxy-2-naphthyl-α-methylacetic acid, an alkyl ester thereof derived from an alkanol having 1 to 12 carbon atoms, or a pharmaceutically acceptable addition salt thereof.

3. The composition according to claim 1 wherein said compound is 6-methoxy-2-naphthyl-α-methylacetic acid.

4. The composition according to claim 1 wherein said compound is d 6-methoxy-2-naphthyl-α-methylacetic acid, an alkyl ester thereof derived from an alkanol having 1 to 12 carbon atoms, or a pharmaceutically acceptable addition salt thereof.

5. The composition according to claim 1 wherein said compound is d 6-methoxy-2-naphthyl-α-methylacetic acid.

6. The composition according to claim 1 wherein said compound is 6-methylthio-2-naphthyl-α-methylacetic acid, an alkyl ester thereof derived from an alkanol having 1 to 12 carbon atoms, or a pharmaceutically acceptable addition salt thereof.

7. The composition according to claim 1 wherein said compound is 6-methylthio-2-naphthyl-α-methylacetic acid.

8. The composition of claim 1 wherein said compound is the sodium salt of 6-methoxy-2-naphthyl-α-methylacetic acid.

9. The composition of claim 1 wherein said compound is the sodium salt of d 6-methoxy-2-naphthyl-α-methylacetic acid.

10. The composition of claim 1 wherein said compound is methyl-6-methoxy-2-naphthyl-α-methylacetate.

11. A method for treating inflammation, pain, pyrexia and pruritus in mammals which comprises administering to a mammal suffering therefrom a therapeutically effective amount of a compound represented by the formula:

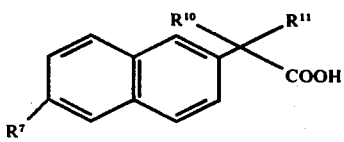

where:
$R^7$ is alkyl having 1 to 6 carbon atoms, cycloalkyl having 3 to 7 carbon atoms, hydroxymethyl, alkoxymethyl having 2 to 7 carbon atoms, trifluoromethyl, vinyl, ethynyl, fluoro, chloro, hydroxy or a conventional hydrolyzable ester thereof derived from a hydrocarbon carboxylic acid having 1 to 12 carbon atoms, alkoxy having 1 to 6 carbon atoms, difluoromethoxy, alkoxymethyloxy having 2 to 7 carbon atoms, alkylthiomethyloxy having 2 to 7 carbon atoms, alkylthio having 1 to 6 carbon atoms, difluoromethylthio, alkoxymethylthio having 2 to 7 carbon atoms, alkylthiomethylthio having 2 to 7 carbon atoms, formyl, carboxy, alkoxycarbonyl having 2 to 7 carbon atoms, acetyl, cyano or phenyl optionally p-monosubstituted with methyl, fluoro, chloro, hydroxy, methoxy or ethyl; one of $R^{10}$ and $R^{11}$ is hydrogen, and the other is methyl, ethyl, difluoromethyl, fluoro or chloro, or $R^{10}$ and $R^{11}$ taken together are alkylidene, halomethylene or ethylene;
an alkyl ester of a compound of formula XIV derived from an alkanol having 1 to 12 carbon atoms; or a pharmaceutically acceptable addition salt thereof.

12. The method according to claim 11 wherein said compound is 6-methoxy-2-naphthyl-α-methylacetic acid, an alkyl ester thereof derived from an alkanol having 1 to 12 carbon atoms, or a pharmaceutically acceptable addition salt thereof.

13. The method according to claim 11 wherein said compound is 6-methoxy-2-naphthyl-α-methylacetic acid.

14. The method according to claim 11 wherein said compound is 6-methylthio-2-naphthyl-α-methylacetic acid, an alkyl ester thereof derived from an alkanol having 1 to 12 carbon atoms, or a pharmaceutically acceptable addition salt thereof.

15. The method according to claim 11 wherein said compound is 6-methylthio-2-naphthyl-α-methylacetic acid.

16. The method according to claim 11 wherein said compound is d 6-methoxy-2-naphthyl-α-methylacetic acid, an alkyl ester thereof derived from an alkanol having 1 to 12 carbon atoms, or a pharmaceutically acceptable addition salt thereof.

17. The method according to claim 11 wherein said compound is d 6-methoxy-2-naphthyl-α-methylacetic acid.

18. The method according to claim 11 wherein said compound is 6-fluoro-2-naphthyl-α-methylacetic acid, an alkyl ester thereof derived from an alkanol having 1 to 12 carbon atoms, or a pharmaceutically acceptable addition salt thereof.

19. The method according to claim 11 wherein said compound is 6-chloro-2-naphthyl-α-methylacetic acid, an alkyl ester thereof derived from an alkanol having 1 to 12 carbon atoms, or a pharmaceutically acceptable addition salt thereof.

20. The method according to claim 11 wherein said compound is 6-methyl-2-naphthyl-α-methylacetic acid, an alkyl ester thereof derived from an alkanol having 1 to 12 carbon atoms, or a pharmaceutically acceptable addition salt thereof.

21. The method according to claim 11 wherein said compound is 6-trifluoromethyl-2-naphthyl-α-methylacetic acid, an alkyl ester thereof derived from an alkanol having 1 to 12 carbon atoms, or a pharmaceutically acceptable addition salt thereof.

22. The method according to claim 11 wherein said compound is 6-difluoromethoxy-2-naphthyl-α-methylacetic acid, an alkyl ester thereof derived from an alkanol having 1 to 12 carbon atoms, or a pharmaceutically acceptable addition salt thereof.

23. The method of claim 11 wherein said compound is the sodium salt of 6-methoxy-2-naphthyl-α-methylacetic acid.

24. The method of claim 11 wherein said compound is the sodium salt of d 6-methoxy-2-naphthyl-α-methylacetic acid.

25. The method of claim 11 wherein said compound is methyl 6-methoxy-2-naphthyl-α-methylacetate.

* * * * *